(12) United States Patent
Yada et al.

(10) Patent No.: US 7,297,814 B2
(45) Date of Patent: Nov. 20, 2007

(54) MULTITUBE REACTOR, VAPOR PHASE CATALYTIC OXIDATION METHOD USING THE MULTITUBE REACTOR, AND START UP METHOD APPLIED TO THE MULTITUBE REACTOR

(75) Inventors: Shuhei Yada, Yokkaichi (JP);
Hirochika Hosaka, Yokkaichi (JP);
Masayasu Goriki, Yokkaichi (JP);
Kimikatsu Jinno, Yokkaichi (JP);
Yasushi Ogawa, Yokkaichi (JP);
Yoshiro Suzuki, Yokkaichi (JP)

(73) Assignee: Mitsubishi Chemical Corporation, Tokyo (JP)

( * ) Notice: Subject to any disclaimer, the term of this patent is extended or adjusted under 35 U.S.C. 154(b) by 486 days.

(21) Appl. No.: 11/049,106

(22) Filed: Feb. 3, 2005

(65) Prior Publication Data
US 2005/0131254 A1    Jun. 16, 2005

Related U.S. Application Data

(60) Division of application No. 10/887,868, filed on Jul. 12, 2004, now Pat. No. 7,144,557, which is a continuation of application No. PCT/JP03/00160, filed on Jan. 10, 2003.

(30) Foreign Application Priority Data

| Jan. 11, 2002 | (JP) | ................................. 2002-4636 |
| Feb. 14, 2002 | (JP) | ............................... 2002-36460 |
| Mar. 14, 2002 | (JP) | ............................... 2002-69820 |
| Apr. 9, 2002 | (JP) | ............................. 2002-105924 |

(51) Int. Cl.
*C07C 51/16* (2006.01)
*C07C 45/00* (2006.01)
*B01J 10/00* (2006.01)
*F28D 7/00* (2006.01)

(52) U.S. Cl. ...................... 562/532; 568/476; 422/196; 422/198; 422/200

(58) Field of Classification Search ...................... None
See application file for complete search history.

(56) References Cited

U.S. PATENT DOCUMENTS

| 4,320,227 A | 3/1982 | Matsumoto et al. |
| 5,006,131 A | 4/1991 | Karafian et al. |
| 5,149,884 A | 9/1992 | Brenner et al. ............. 568/471 |
| 5,677,261 A | 10/1997 | Tenten et al. ................ 502/439 |
| 5,772,870 A | 6/1998 | Basse |
| 6,057,481 A | 5/2000 | Brockwell et al. |
| 6,069,271 A | 5/2000 | Tanimoto et al. |
| 6,563,000 B1 | 5/2003 | Yunoki et al. |
| 6,582,667 B1 | 6/2003 | Ogata et al. |
| 6,808,689 B1 | 10/2004 | Matsumoto et al. |
| 6,946,573 B2 | 9/2005 | Matsumoto et al. |
| 7,144,557 B2 * | 12/2006 | Yada et al. ................. 422/196 |
| 2003/0065194 A1 | 4/2003 | Weiguny et al. |

FOREIGN PATENT DOCUMENTS

| CN | 1277955 | 12/2000 |
| CN | 1289634 A | 4/2001 |
| CN | 1323779 A | 11/2001 |
| DE | 2140125 | 2/1972 |
| JP | 62-201646 | 9/1987 |
| JP | 63-054941 | 3/1988 |
| JP | 6-13096 | 2/1994 |
| JP | 6-38918 | 5/1994 |
| JP | 8-92147 | 4/1996 |
| JP | 10-72389 | 3/1998 |
| JP | 11-130722 | 5/1999 |
| JP | 2000-93784 | 4/2000 |
| JP | 2001-310123 | 11/2001 |
| RU | 93008579 | 3/1995 |
| RU | 95117124 | 9/1997 |
| WO | 01/68626 | 9/2001 |

* cited by examiner

*Primary Examiner*—Sikarl A. Witherspoon
(74) *Attorney, Agent, or Firm*—Wenderoth, Lind & Ponack, L.L.P.

(57) ABSTRACT

A multitube reactor, wherein tubes having smaller tolerance between a nominal size and actual sizes are used as reaction tubes to stably perform a high yield reaction for a long period, a catalyst is filled into the reaction tubes so that the catalyst layer peak temperature portions of the reaction tubes are not overlapped with the connection sites thereof with baffles to effectively prevent hot spots from occurring and stably perform a reaction for a long period without the clogging of the reaction tubes, a heat medium and raw material gas are allowed to flow in the direction of a countercurrent and a specified type of catalyst is filled into the reaction tubes so that activity is increased from the inlet of the raw material gas to the outlet thereof to prevent the autooxidation of products so as to prevent equipment from being damaged due to the reaction, and, at the time of starting, gas with a temperature of 100 to 400° C. is led to the outside of the reaction tubes to increase the temperature of the reaction tubes and, a heat medium, which is solid at the room temperature, is heated to circulate to the outside of the reaction tubes to efficiently start up the reactor without affecting the activity of the catalyst.

12 Claims, 10 Drawing Sheets

MULTITUBE REACTOR, VAPOR PHASE CATALYTIC OXIDATION METHOD USING THE MULTITUBE REACTOR, AND START UP METHOD APPLIED TO THE MULTITUBE REACTOR

This is a divisional of Ser. No. 10/887,868, filed Jul. 12, 2004 now U.S. Pat. No. 7,144,557, which is a continuation of International Application No. PCT/JP03/00160 filed Jan. 10, 2003.

TECHNICAL FIELD

The present invention relates to a multitube reactor applied to a method of producing (meth)acrolein and/or (meth)acrylic acid by oxidizing propylene, propane, isobutylene, isobutanol, or t-butanol with a molecular oxygen-containing gas, a vapor phase catalytic oxidation method using the multitube reactor, and to a start up method applied to the multitube reactor.

BACKGROUND ART

A conventional multitube reactor is equipped with a plurality of reaction tubes having a catalyst packed therein and a plurality of baffles inside a shell for feeding and circulating inside the shell a fluid for heat removal (hereinafter, referred to as "heat medium") introduced into the shell. A raw material gas fed inside the reaction tubes reacts in the presence of the catalyst inside the reaction tubes, to thereby generate heat of reaction. The heat of reaction is removed by a heat medium circulating inside the shell.

When differences of inner volumes among the plurality of reaction tubes equipped inside the shell is large, amounts of the catalyst packed inside the reaction tubes are irregular and a scatter arises. As a result, a flow rate of the raw material gas fed or a retention time differs among the reaction tubes, thereby becoming a factor causing yield reduction of a target product and reduced catalyst life. Further, a localized abnormal high-temperature site (hot spot) may form in the reaction tubes provoking a reaction out of control, thereby causing a problem of inhibiting a continuous operation.

Further, in a multitube reactor provided with the baffles, the heat medium does not flow at all in a portion where the baffles and the reaction tubes are fixed to each other when the baffles and the reaction tubes are fixed through welding, flanges, or the like. A reactor in which outer walls of the reaction tubes and the baffle are not fixed also exists, but the amount of the heat medium flowing through this clearance is limited. The following problems arise in a vapor phase catalytic oxidation method using a fixed bed multitube heat-exchanger type reactor as described above.

There is a state of poor heat removal in the reaction tubes in a portion where flow of the heat medium is insufficient inside the shell. A localized abnormal high-temperature zone (hot spot) may form in the reaction tubes which are in a state of poor heat removal, possibly resulting in a reaction out of control. Further, a reaction may not become out of control, but problems arise including ease of clogging the reaction tubes, yield reduction of the reaction product gas, deterioration of the catalyst life, and inhibition of a stable operation for a long period of time.

Many methods of suppressing hot spot formation have been proposed for the multitube reactor used in a vapor phase catalytic oxidation reaction. For example, JP 08-092147 A discloses a method of providing uniform heat medium temperature by: setting a flow direction of a reactant gas guided to a reactor and that of the heat medium inside a shell in a countercurrent; allowing the heat medium to flow further upward in a meandering way using baffles; and adjusting temperature differences of the heat medium from an inlet of the reactor to an outlet thereof within 2 to 10° C. or less.

The multitube reactor generally consists of a plurality of tubes (bundle) arranged vertically, and thus a process fluid flow can be upflow or downflow by allowing a process fluid to flow from an upper portion or lower portion of the reactor. The heat medium can also be fed to the shell from the upper portion or lower portion thereof.

Therefore, the multitube reactor is classified into two types similar to a general shell and tube heat exchanger: a concurrent type allowing the process fluid and the heat medium to flow in the same direction; and a countercurrent type allowing the process fluid and the heat medium to flow in opposite directions.

Further, the multitube reactor may be classified into the following types considering the directions of the fluids: 1) a concurrent type of downflow process fluid/downflow heat medium; 2) a concurrent type of upflow process fluid/upflow heat medium; 3) a countercurrent type of upflow process fluid/downflow heat medium; and 4) a countercurrent type of downflow process fluid/upflow heat medium.

Proposed in JP 2000-093784 A is a method of suppressing hot spot formation by: allowing a raw material gas and a heat medium to flow in downward concurrent; and preventing a gas reservoir free of the heat medium. Further, the method allows an exchange of a catalyst in a vicinity of a catalyst layer inlet alone where most easily deteriorates by: feeding the raw material gas from an upper portion of a reactor; and allowing the raw material gas to flow downward inside the catalyst layer of reaction tubes.

However, the heat medium and the process fluid move in a concurrent according to the method, and gas temperature in an outlet portion of the reactor increases. Thus, the method has a fault that high concentration of a product (meth)acrolein easily causes an autooxidation reaction (autolysis reaction).

Further, with respect to the upflow, in a method of allowing the process fluid and the heat medium to flow in a concurrent, that is in the same direction, heat medium temperature increases with heat of reaction. Thus, high temperature at a process outlet causes autooxidation at the reactor outlet easily. The autooxidation reaction results in problems of a combustion reaction of the product, equipment breakdown due to temperature increase, and yield reduction.

Proposed is a method of preventing autooxidation for a purpose of preventing temperature increase, by providing a cooling zone or heat exchanger in a downstream of a reaction portion for decreasing gas temperature. However, in a concurrent, heat medium temperature in the vicinity of the reactor outlet and process gas temperature in an outlet portion are high. Thus, an amount of heat removal becomes large and a cooling portion (cooling zone and heat exchanger) enlarges, thereby becoming disadvantageous in point of cost.

Further, even if a significant autooxidation reaction is not caused, an autooxidation reaction is caused by a part of a product, which arises a problem of yield reduction of a target product as a whole.

Further, in a shell-tube type reactor circulating a heat medium which is solid at normal temperature, there is a necessary to maintain the heat medium at temperature of the solidifying point or above to ensure fluidity thereof for circulating the heat medium inside the reactor.

JP 2001-310123 A discloses a-reactor start up method for a multitube reactor having reaction tubes, an introducing port of a fluid flowing outside reaction tubes, and a discharging port thereof for removing heat generated inside the reaction tubes, the method being characterized by including: heating reaction tubes by introducing a gas having temperature of 100 to 400° C. in the reaction tubes; and circulating a heated heat medium through the outside of the reaction tubes. Further, a gas not providing an effect when being mixed with a catalyst packed in the reaction tubes or with a raw material gas (such as air) is selected as the gas introduced to the reaction tubes.

However, a large volume of a high temperature gas is introduced to the reaction tubes according to the above-mentioned method, thereby changing an oxidation state of the catalyst. Therefore, catalytic activity and selectivity may be affected, possibly resulting in yield reduction or reduced catalyst life.

DISCLOSURE OF THE INVENTION

A first object of the present invention is to provide a multitube reactor for improving life of a catalyst packed inside the reaction tubes and for preventing yield reduction of a target product.

Further, a second object of the present invention is to provide a vapor phase catalytic oxidation method comprising: using the above-mentioned multitube reactor; circulating a heat medium through the outside of the reaction tubes; and feeding a reaction raw material gas inside the reaction tubes packed with a catalyst to obtain a reaction product gas, in which hot spot formation can be effectively prevented, the reaction tubes are not clogged, an yield of a reaction product gas is high, a catalyst life is long, and a stable operation can be performed over a long period of time.

Further, a third object of the present invention is to reduce process gas temperature at a product discharging port of the reactor in the vapor phase catalytic oxidation method using the multitube reactor described above.

Further, a fourth object of the present invention is to provide a method which makes a reactor start up effectively without adversely affecting the catalytic activity in a shell-tube type reactor of circulating a heat medium which is solid at normal temperature, the method being applied to a multitube reactor such as the above-mentioned multitube reactor.

The present invention provides a multitube reactor represented by the following items (1) to (3) (hereinafter, may also be referred to as "multitube reactor of the present invention") as a means for solving at least the first object of the present invention.

(1) A multitube reactor comprising a plurality of reaction tubes having a catalyst packed therein, and a shell equipped with the reaction tubes inside and into which a heat medium flowing outside the reaction tubes is introduced, wherein the reaction tubes are selected from tubes having same nominal outside diameter and same nominal wall-thickness, an outside diameter tolerance of ±0.62%, and a wall-thickness tolerance of +19% to −0%.

(2) The multitube reactor comprising a plurality of reaction tubes having a catalyst packed therein, and a shell equipped with the reaction tubes inside and into which a heat medium flowing outside the reaction tubes is introduced, wherein the reaction tubes are selected from tubes having same nominal outside diameter and same nominal wall-thickness, an outside diameter tolerance of ±0.56%, and a wall-thickness tolerance of +17% to −0%.

(3) The multitube reactor according to the above item (1) or (2), which is used for production of (meth)acrolein and/or (meth) acrylic acid by oxidizing propylene, propane, isobutylene, isobutanol, or t-butanol with a molecular oxygen-containing gas.

Further, the present invention provides a vapor phase catalytic oxidation method represented by the following items (4) to (6) using the multitube reactor of the present invention for solving at least one of the second, third, and fourth objects of the present invention.

(4) A vapor phase catalytic oxidation method comprising: using the multitube reactor according to the above items (1) or (2), which further comprises baffles connected to the reaction tubes through connecting sites for changing a flow path of a heat medium introduced into the shell; circulating the heat medium through the outside of the reaction tubes; and feeding a reaction raw material gas inside the reaction tubes packed with a catalyst to obtain a reaction product gas,; wherein the method comprises setting catalyst packing specifications in the reaction tubes so that catalyst layer peak temperature sites of the reaction tubes are not located at the connecting sites between the baffles and the reaction tubes.

(5) The vapor phase catalytic oxidation method according to the above item (4), wherein the method comprises: packing the reaction tubes with a Mo—Bi catalyst and/or Sb—Mo catalyst so that an activity increases from a process gas inlet to a process gas outlet of the reaction tubes; allowing the heat medium and the process gas to flow in a countercurrent; and oxidizing propylene, propane, or isobutylene, and/or (meth)acrolein through vapor phase catalytic oxidation with a molecular oxygen-containing gas.

(6) The vapor phase catalytic oxidation method according to the above item (4) or (5), wherein the method comprises: heating the reaction tubes through introduction of a gas having temperature of 100 to 400° C. outside the reaction tubes; and circulating the heat medium which is solid at normal temperature outside the heated reaction tubes to start up the multitube reactor.

Further, the present invention provides a vapor phase catalytic oxidation method (hereinafter, may also be referred to as "first vapor phase catalytic oxidation method") represented by the following items (7) to (10) for solving at least the second object of the present invention.

(7) A vapor phase catalytic oxidation method comprising: using a fixed bed multitube heat-exchanger type reactor having a plurality of reaction tubes and baffles connected to the reaction tubes through connecting sites for changing a flow path of a heat medium flowing outside the reaction tubes; circulating the heat medium through the outside of the reaction tubes; feeding a reaction raw material gas inside the reaction tubes packed with a catalyst to obtain a reaction product gas,, wherein the method comprises setting catalyst packing specifications in the reaction tubes so that catalyst layer peak temperature sites of the reaction tubes are not located at the connecting sites between the baffles and the reaction tubes.

(8) The vapor phase catalytic oxidation method according to the above item (7), wherein layers having different catalyst packing specifications are provided with two or more catalyst in one reaction tube.

(9) The vapor phase catalytic oxidation method according to the above item (7) or (8), wherein items for setting the catalyst packing specifications comprise a type of catalyst, an amount of catalyst, a form of catalyst, a method for diluting the catalyst, and lengths of reaction zones.

(10) The vapor phase catalytic oxidation method according to any one of the above items (7) to (9), wherein the method comprises oxidizing propane, propylene, and/or isobutylene with molecular oxygen through the vapor phase catalytic oxidation method to produce (meth) acrylic acid.

Further, the present invention provides a vapor phase catalytic oxidation method (hereinafter, may also be referred to as "second vapor phase catalytic oxidation method") represented by the following items (11) and (12) for solving at least the third object of the present invention.

(11) A vapor phase catalytic oxidation method comprises: using a multitube reactor which comprises: a cylindrical shell having a raw material feed port and a product discharging port; a plurality of ring-shaped tubes arranged on an outer periphery of the cylindrical shell for introducing or discharging a heat medium into or from the cylindrical shell; a circulating device connecting the plurality of the ring-shaped tubes one another; a plurality of reaction tubes restrained by a plurality of tube plates of the reactor and comprising a catalyst; and a plurality of baffles provided in a longitudinal direction of the reactor and for changing a direction of the heat medium introduced into the cylindrical shell; oxidizing propylene, propane, or isobutylene, and/or (meth)acrolein through vapor phase catalytic oxidation with a molecular oxygen-containing gas to obtain (meth)acrolein and/or (meth)acrylic acid,; wherein the method comprises, packing a Mo—Bi catalyst and/or Sb—Mo catalyst in the reaction tubes so that an activity increases from a process gas inlet to a process gas outlet of the reaction tubes; and allowing the heat medium and the process gas to flow in a countercurrent.

(12) The vapor phase catalytic oxidation method according to the above item (11), wherein the Mo—Bi catalyst is represented by the following general formula (I) and the Sb—Mo catalyst is represented by the following general formula (II):

$$Mo_a W_b Bi_c Fe_d A_e B_f C_g D_h E_i O_j \quad (I)$$

(wherein, Mo represents molybdenum; W represents tungsten; Bi represents bismuth; Fe represents iron; A represents at least one type of element chosen from nickel and cobalt; B represents at least one type of element selected from the group consisting of sodium, potassium, rubidium, cesium, and thallium; C represents at least one type of element selected from alkaline earth metals; D represents at least one type of element selected from the group consisting of phosphorus, tellurium, antimony, tin, cerium, lead, niobium, manganese, arsenic, boron, and zinc; E represents at least one type of element selected from the group consisting of silicon, aluminum, titanium, and zirconium; O represents oxygen; a, b, c, d, e, f, g, h, i, and j represent atomic ratios of Mo, W, Bi, Fe, A, B, C, D, E, and O respectively; and if a=12, $0 \leq b \leq 10$, $0<c \leq 10$, $0<d \leq 10$, $2 \leq e \leq 15$, $0<f \leq 10$, $0 \leq g \leq 10$, $0 \leq h \leq 4$, and $0 \leq i \leq 30$; and j is a value determined from oxidation states of the respective elements); and

$$Sb_k Mo_l (V/Nb)_m X_n Y_p Si_q O_r \quad (II)$$

(wherein, Sb represents antimony; Mo represents molybdenum; V represents vanadium; Nb represents niobium; X represents at least one type of element selected from the group consisting of iron (Fe), cobalt (Co), nickel (Ni), and bismuth (Bi); Y represents at least one type of element chosen from copper (Cu) and tungsten (W); Si represents silicon; O represents oxygen; (V/Nb) represents V and/or Nb; k, l, m, n, p, q, and r represent atomic ratios of Sb, Mo, (V/Nb), X, Y, Si, and O respectively; and $1 \leq k \leq 100$, $1 \leq l \leq 100$, $0.1 \leq m \leq 50$, $1 \leq n \leq 100$, $0.1 \leq p \leq 50$, $1 \leq q \leq 100$; and r is a value determined from oxidation states of the respective elements).

Further, the present invention provides a method for starting up (hereinafter, may also be referred to as "start up method of the present invention") represented by the following items (13) and (14) for solving at least the fourth object of the present invention.

(13) A start up method for a shell-tube type reactor having a system of circulating a heat medium which is solid at normal temperature, the shell-tube type reactor having reaction tubes, and an introducing port and discharging port of a fluid flowing outside the reaction tubes for removing heat generated inside the reaction tubes, wherein the method comprises:

heating the reaction tubes through introduction of a gas having temperature of 100 to 400° C. outside the reaction tubes; and circulating the heated heat medium through the outside of the reaction tubes.

(14) The start up method according to the above item (13), wherein the heat medium which is solid at normal temperature has a solidifying point of 50 to 250° C.

Hereinafter, the present invention will be described in more detail.

<Multitube Reactor of the Present Invention>

A multitube reactor of the present invention is a multitube reactor equipped with a plurality of reaction tubes inside a shell of the multitube reactor, the plurality of reaction tubes being selected from tubes having the same nominal outside diameter and the same nominal wall-thickness, an outside diameter tolerance of ±0.62% and a wall-thickness tolerance of +19% to −0%, particularly preferably an outside diameter tolerance of ±0.56% and a wall-thickness tolerance of +17% to −0%. The multitube reactor is suitably used in oxidizing propylene, propane, isobutylene, isobutanol, or t-butanol with a molecular oxygen-containing gas.

In the multitube reactor of the present invention, the phrase "the same nominal outside diameter and the same nominal wall-thickness" means that "in a reaction tube, a nominal outside diameter and an actual outside diameter are substantially the same and a nominal wall-thickness and an actual wall-thickness are substantially the same". In addition, the above-mentioned range of the tolerance is defined in the present invention as the range which represents "substantially the same". The actual dimensions of a reaction tube can be measured by means of a conventionally known method. The dimensions may adopt the measured value at a given position or the average value of a plurality of measured values.

An outline of the multitube reactor of the present invention will be described with reference to FIG. 1.

Reference numeral 2 represents a shell of the multitube reactor, and the shell 2 comprises reaction tubes 1a, 1b, and 1c each packed with a catalyst, the reaction tubes being fixed by both a lower tube plate 5b and an upper tube plate 5a.

The reaction tubes 1a, 1b, and 1c each have an inner diameter of about 20 to 40 mmΦ, a wall-thickness of 1 to 2 mm, and a length of 3,000 to 6,000 mm. A carbon steel tube or stainless steel tube is used as a material for each of the reaction tubes 1a, 1b, and 1c.

The total number of the reaction tubes 1a, 1b, and 1c equipped inside the shell 2 varies depending on the amount of production of a target product but: is typically 1,000 to 30,000. The arrangement of the tubes varies depending on outside diameter sizes of the reaction tubes, but the reaction tubes equipped inside the shell at intervals of 5 to 50 mm to establish a square arrangement or an equilateral triangle arrangement.

The above equilateral triangle arrangement is often used because the arrangement can increase the number of the reaction tubes 1a, 1b, and 1c equipped inside the reactor per unit area.

The outside diameter tolerance and wall-thickness tolerance of each of the reaction tubes used in the present invention are far more rigorous than the tolerance of JIS or of ASTM, and such tubes that satisfy the rigorous tolerances are used.

That is, each of the reaction tubes is desirably selected from tube products having the same nominal outside diameter and the same nominal wall-thickness, an outside diameter tolerance of ±0.62% and a wall-thickness tolerance of +19% to −0%, particularly preferably an outside diameter tolerance of ±0.56% and a wall-thickness tolerance of +17% to −0%. In the multitube reactor of the present invention, all the reaction tubes equipped inside the multitube reactor preferably satisfy the above conditions. However, it is sufficient that at least 95%, more preferably at least 99% of the tubes satisfy the above conditions.

The shell 2 has, at its top and bottom ends, inlet and outlet portions 4a and 4b for a raw material gas Rg for a reaction, and the raw material gas Rg flows through the reaction tubes 1a, 1b, and 1c in an upward or downward flow direction via the inlet and outlet portions 4a and 4b for the raw material gas arranged on the top and bottom ends of the reactor. The flow direction of the raw material gas is not particularly limited, but is more preferably a downflow.

In addition, a ring-shaped tube 3a for introducing a heat medium Hm is arranged on the outer periphery of the shell 2. The heat medium Hm pressurized by a circulating pump 7 is introduced into the shell 2 through the ring-shaped tube 3a.

The heat medium Hm introduced into the shell 2 flows upward while changing its flow direction as indicated by arrows due to baffles 6a, 6b, and 6a equipped inside in the shell 2. During this period, the heat medium Hm contacts the outer surfaces of the reaction tubes 1a, 1b, and 1c to remove heat of reaction, and then returns to the circulating pump 7 via the ring-shaped tube 3a arranged on the outer periphery of the shell 2.

Part of the heat medium Hm absorbing the heat of reaction flows toward a discharge tube 8b arranged on an upper portion of the circulating pump 7 to be cooled by a heat exchanger (not shown). Then, the heat medium is sucked again in the circulating pump 7 through a heat medium feed tube 8a to be introduced into the shell 2.

The temperature of the heat medium Hm introduced into the shell 2 is controlled by adjusting the temperature or quantity of flow of the heat medium flowing from the heat medium feed tube 8a. In addition, the temperature of the heat medium Hm is measured with a thermometer 14 inserted into the side of the inlet of the ring-shaped tube 3a.

An inner body plate of each of the ring-shaped tube 3a and a ring-shaped tube 3b is equipped with a flow-rectifying plate (not shown) in order to minimize the flow rate distribution of the heat medium in a circumferential direction. A porous plate or a plate with slits is used for the flow-rectifying plate. The flow-rectifying plate is arranged in such a manner that the same quantity of flow of the heat medium Hm is introduced into the shell 2 at the same flow rate from the entire circumference by changing an opening area of the porous plate or by changing slit intervals.

In addition, the temperature inside the ring-shaped tube 3a, preferably the temperature inside each of the ring-shaped tubes 3a and 3b, can be monitored with a plurality of thermometers 15 arranged at even interval along the circumference as shown in FIG. 4. 1 to 5 baffles are typically equipped inside the shell 2. In FIG. 1, 3 baffles (6a, 6b, and 6a) are equipped inside the shell 2. The presence of those baffles causes the flow of the heat medium Hm in the shell 2 to center on the central portion from the outer peripheral portion of the shell 2, to flow upward through an opening of the baffle 6a toward the outer peripheral portion while changing its direction, and then to reach the inner wall of the shell 2.

Then, the heat medium Hm changes its direction again to converge to the central portion while flowing upward through a gap between the inner wall of the shell 2 and the outer periphery of the baffle 6b. Finally, the heat medium Hm flows upward through an opening of the baffle 6a toward the outer periphery along the bottom face of the upper tube plate 5a in the shell 2 to be introduced into the ring-shaped tube 3b. After that, the heat medium Hm is sucked in the circulating pump 7 to be circulated in the shell 2 again.

The specific structure of a baffle used in the present invention may be any one of a segment-type noncircular baffle shown in FIG. 2 and a disc-type baffle shown in FIG. 3.

Both types of baffles have the same relationship between the flow direction of a heat medium and the axis of a reaction tube.

The baffle 6a has its outer periphery on the inner wall of the shell 2 and has an opening around its center. In addition, the outer periphery of the baffle 6b is smaller than the circumference of the inner wall of the shell 2 so that a gap is formed between the outer periphery of the baffle 6b and the inner wall of the shell 2.

The heat medium changes its direction at each opening and gap while moving upward, and the flow rate is changed.

Thermometers 11 are equipped inside the reaction tubes 1a, 1b, and 1c, which are equipped inside in the shell 2. Signals are transmitted from thermometers to the outside of the shell 2 to measure the temperature distribution of a catalyst layer packed inside a reaction tube in an axial direction of the reaction tube.

A plurality of thermometers 11 are inserted into the reaction tubes 1a, 1b, and 1c to measure temperatures at 2 to 20 points in an axial direction.

The reaction tubes 1a, 1b, and 1c equipped inside the shell 2 are divided by the 3 baffles 6a, 6b, and 6c, and are classified into 3 types depending on the relationship with the flow direction of the heat medium Hm.

That is, the reaction tube 1a is connected to the baffle 6b. Therefore, the flow direction of the heat medium Hm is restrained only by the baffle 6b. In addition, the flow direction is not restrained by the other two baffles 6a because the reaction tube 1a penetrates through opening portions of the two baffles 6a.

The direction of the heat medium Hm introduced into the shell 2 through the ring-shaped tube 3a is changed as indicated by an arrow shown in FIG. 1 at the central portion of the shell 2. Furthermore, the reaction tube 1a is located at the position where the direction is changed, and thus the heat medium Hm that flows along the outer periphery of the reaction tube 1a mainly flows in parallel with the axis of the reaction tube 1a.

The reaction tube 1b is connected to the 3 baffles 6a, 6b, and 6a so that the flow direction of the heat medium Hm is restrained by each of the baffles. In addition, the heat medium Hm flowing along the outer periphery of the reaction tube 1b flows at a right angle with the axis of the reaction tube 1b at nearly all positions of the reaction tube 1b. It should be noted that most of the reaction tubes equipped inside the shell 2 are located at the position of the reaction tube 1b.

In addition, the reaction tube 1c is not connected to the baffle 6b and penetrates through a gap between the outer periphery of the baffle 6b and the inner wall of the shell 2. Therefore, the flow of the heat medium Hm is not restrained by the baffle 6b at this position and is parallel with the axis of the reaction tube 1c.

FIG. 4 shows the positional relationship among the reaction tubes 1a, 1b, and 1c and the baffles 6a, 6b, and 6a, and the correlation of the flow of the heat medium Hm.

When an opening portion (the most inner circle indicated by broken lines) of the baffle 6a is located at a converging position of the heat medium Hm, that is, the center of the shell 2, the flow of the heat medium Hm is parallel with-the reaction tube 1a. Moreover, nearly no heat medium Hm flows particularly at the center of the opening portion of the baffle 6a, and the flow rate is close to zero. In other words, heat transfer efficiency is extremely poor. Therefore, the reaction tube 1a is not provided at this position in some cases.

FIG. 5 shows another-example of the present invention in which the shell 2 of the reactor is divided by an intermediate tube plate 9.

Different heating media Hm1 and Hm2 are circulated in spaces obtained by dividing the shell 2 and the temperatures of the media are separately controlled.

A raw material gas Rg is introduced through a raw material gas inlet 4a of the shell and is successively reacted to yield a product.

Heat media having different temperatures are present in the shell, and hence how each of the reaction tubes 1a, 1b, and 1c is packed with a catalyst is as follows. In a case (i), each reaction tube is entirely packed with the same catalyst and the temperature of the catalyst is changed at the inlet and outlet of the shell to allow a reaction. In a case (ii), a catalyst is packed at the inlet portion. For rapidly cooling a reaction product, no catalyst is packed at the outlet portion, that is, the outlet portion serves as a cavity or is packed with an inert substance without reaction activity. In a case (iii), different catalysts are packed at the inlet and outlet portions. For rapidly cooling a reaction product, no catalyst is packed at an intermediate portion or is packed with an inert substance without reaction activity.

For example, when propylene or isobutylene is introduced as a mixed gas with a molecular oxygen-containing gas, propylene or isobutylene is converted into (meth)acrolein at an upper portion and is oxidized to (meth)acrylic acid at a lower portion.

Different catalysts are packed in upper and lower portions in each of the reaction tubes 1a, 1b, and 1c, and the temperatures of the catalysts are controlled to respective optimum temperatures, to thereby carry out a reaction. An inert substance layer that is not involved in the reaction may be present as a partition between the upper portion and the lower portion. In the case, the inert substance layer is provided in a portion corresponding to the position at which the outer periphery of each of the reaction tubes 1a, 1b, and 1c is connected to the intermediate tube plate 9.

In FIG. 6, reference numeral 9 represents an intermediate tube plate, and 3 thermal shields 10 are fixed at the bottom face of the intermediate tube plate 9 by spacer rods 13.

As shown in the figure, 2 to 3 thermal shields 10 are provided within 100 mm below or above the intermediate tube plate 9, whereby preferably forming a flowless stagnant space 12 filled with the heat medium Hm1 or Hm2, to provide a heat insulation effect.

Thermal shields 10 are attached to the intermediate tube plate 9 for the following reason. That is, in FIG. 5, when the difference in controlled temperature between the heat medium Hm1 introduced into the lower portion of the shell 2 and the heat medium Hm2 introduced into the upper portion of the shell 2 exceeds 100° C., heat transfer from the high-temperature heat medium to the low-temperature heat medium cannot be neglected. Thus, the precision in controlling the reaction temperature of a catalyst may degrade at lower temperatures. In such a case, heat insulation is necessary to prevent heat transfer above and/or below the intermediate tube plate 9.

Here, the types and ratios of raw material gas components and the importance of uniform packing of a catalyst will be described.

Introduced into a multitube reactor for use in vapor phase catalytic oxidation is a mixed gas of propylene or isobutylene and/or (meth)acrolein with a molecular oxygen-containing gas or with water vapor as a raw material gas Rg for a reaction.

The concentration of propylene or isobutylene ranges from 3 to 10 vol %. A molar ratio of oxygen to propylene or to isobutylene ranges from 1.5 to 2.5, and a molar ratio of water vapor to propylene or to isobutylene ranges from 0.8 to 2.0.

The introduced raw material gas Rg is distributed to the reaction tubes 1a, 1b, and 1c and then flows through each reaction tube to react by an oxidation catalyst packed inside each reaction tube. However, the distribution of the raw material gas Rg to each reaction tube is affected by the packing weight, packing density, and the like of a catalyst in a reaction tube. The packing weight, packing density, and the like are set at the time of packing a catalyst into a reaction tube. Therefore, it is essential to uniformly pack a catalyst into each reaction tube.

To uniformize the weight of a catalyst packed inside each reaction tube, it is important to set a rigorous tolerance of a reaction tube into which a catalyst is packed.

The raw material gas Rg flowing through each of the reaction tubes 1a, 1b, and 1c is initially heated to a reaction starting temperature while flowing through the inert substance layer packed at the inlet portion.

The raw material (propylene or isobutylene) is oxidized by the catalyst packed as the successive layer in the reaction tube, and the temperature of the raw material further increases by heat of reaction.

The reaction weight in the inlet portion of the catalyst layer is most. The heat of reaction generated increases the temperature of the raw material gas Rg when the heat of reaction is greater than the quantity of heat removal by the heat medium Hm. In such a case, hot spots may be formed. The hot spots are often formed at a position 300 to 1,000 mm from the inlet of each of the reaction tubes 1a, 1b, and 1c.

Here, the effect of the heat of reaction generated on a catalyst, the temperature of a heat medium and the allowable maximum temperature of hot spots when producing acrolein through an oxidation reaction of propylene with a molecular oxygen-containing gas, the type of heat medium used, and the effect of a fluid state of the heat medium on the heat removal efficiency of the heat medium will be described.

When the heat of reaction generated exceeds the heat removal capacity of the heat medium Hm on the outer periphery of the corresponding reaction tube, the temperature of the raw material gas Rg further increases, and the heat of reaction also increases. Finally, the reaction becomes out of control. In this case, the temperature of the catalyst exceeds the allowable maximum temperature, so that the catalyst undergoes a qualitative change. This change may be a main cause for the deterioration or breakage of the catalyst.

A description is given by taking as an example a former stage reactor (for instance, the portion of the reactor above the intermediate tube plate 9 in FIG. 5) in which acrolein is produced through an oxidation reaction of propylene with a molecular oxygen-containing gas. In this example, the temperature of the heat medium Hm is in the range of 250 to 350° C. and the allowable maximum temperature of the hot spots is in the range of 400 to 500° C.

In addition, the temperature of the heat medium Hm in a latter stage reactor (for instance, the portion of the reactor below the intermediate tube plate 9 in FIG. 5) in which acrolein is oxidized by a molecular oxygen-containing gas to yield acrylic acid is in the range of 200 to 300° C. and the allowable maximum temperature of the hot spots is in the range of 300 to 400° C.

Niter, a mixture of nitrates, is often used as the heat medium Hm that flows inside the shell 2 surrounding the reaction tubes 1a, 1b, and 1c. However, a phenyl ether heat medium of an organic liquid system may also be used.

The heat medium Hm flows to remove heat from the outer periphery of each of the reaction tubes 1a, 1b, and 1c. However, the heat medium Hm introduced into the shell 2 through the ring-shaped tube 3a for heat medium introduction flows toward the central portion from the outer peripheral portion of the shell 2 at a position and reverses its flow direction at another position. Heat removal effects at the positions were found to extremely differ from each other.

A heat transfer coefficient of the heat medium when the flow direction of the heat medium Hm is at a right angle with the axis of a reaction tube is in the range of 1,000 to 2,000 W/m$^{2}$° C. When the flow direction is not at a right angle with the axis of a reaction tube, the heat transfer coefficient varies depending on the flow rate and on whether the flow is an upflow or a downflow. However, the heat transfer coefficient often falls within a narrow range of 100 to 300 W/m$^{2}$° C. when niter is used as the heat medium.

On the other hand, the heat transfer coefficient of a catalyst layer in each of the reaction tubes 1a, 1b, and 1c naturally dependents on the flow rate of the raw material gas Rg, but is about 100 W/m$^{2}$° C. As a matter of course, the rate determining factor of heat transfer is a gas phase in a tube as usual.

Specifically, heat transfer resistance on the outer periphery of each of the reaction tubes 1a, 1b, and 1c when the flow of the heat medium Hm is at a right angle with the axis of the tube is 1/10 to 1/20 that of the gas Rg in the tube. Therefore, a change in flow rate of the heat medium Hm hardly affects the overall heat transfer resistance.

However, when niter flows in parallel with the axis of a tube, the heat transfer coefficient in each of the reaction tubes 1a, 1b, and 1c is comparable to that outside the reaction tubes 1a, 1b, and 1c. Therefore, the effect of the fluid state at the outer periphery of the tube on the heat removal efficiency is large. That is, when the heat transfer resistance at the outer periphery of a tube is 100 W/m$^{2}$° C., the overall heat transfer coefficient becomes half. Furthermore, half the change in heat transfer resistance at the outer periphery of the tube affects the overall heat transfer coefficient.

In each of FIGS. 1 and 5, the flow direction of the heat medium Hm in the shell 2 is represented as an upflow by arrows. However, the present invention can also be applied to the opposite flow direction.

In determining the direction of a circulation flow of the heat medium Hm, a phenomenon of engulfing, in the heat medium flow, a gas that may be present at top ends of the shell 2 and the circulating pump 7, in particular an inert gas such as nitrogen, must be prevented.

In the case where the heat medium Hm is an upflow as shown in FIG. 1, a cavitation phenomenon occurs in the circulating pump 7 when a gas is engulfed at an upper portion of the circulating pump 7. In the worst case, the pump may break.

In the case where the heat medium Hm is a downflow, a gas engulfing phenomenon occurs also at an upper portion of the shell 2. In this case, a stagnant portion of a gas phase is formed at an upper portion of the shell 2, and an upper portion of a reaction tube corresponding to the gas stagnant portion is not cooled by the heat medium Hm.

Prevention of gas stagnation must include: providing a degas line; and replacing a gas of the gas phase with the heat medium Hm. To achieve this, the pressure of the heat medium in the heat medium feed tube 8a is increased and the heat medium discharging tube 8b is provided at the highest position as possible to increase the pressure in the shell 2. The heat medium discharging tube 8b is provided at least above the upper tube plate 5a.

The raw material gas Rg can be an upflow or a downflow in the reaction tubes 1a, 1b, and 1c. However, the raw material gas Rg preferably in a countercurrent in relation to the heat medium flow.

Examples of a method of adjusting activity of a catalyst layer include: a method of adjusting catalyst compositions to use catalysts having different activities; and a method of adjusting activity by mixing catalyst particles with inert substance particles to dilute the catalyst.

A catalyst layer having a small ratio of the catalyst particles is packed into an inlet portion of each of the reaction tubes 1a, 1b, and 1c. A catalyst layer having a large ratio of the catalyst particles or catalyst layer not diluted is packed into a portion of the reaction tube, the portion located downstream with respect to the flow direction of the raw material gas. Although the degree of dilution varies by a catalyst, a (catalyst particles/inert substance particles) mixing ratio is preferably in the range of 7/3 to 3/7 in the former stage and in the range of 10/0 to 5/5 in the latter stage. 2 to 3 stages are typically adopted for the activity change or dilution of a catalyst.

Dilution ratios of the catalysts packed inside the reaction tubes 1a, 1b, and 1c do not need to be the same with each other. For example, the reaction tube 1a has a high maximum temperature so that there is a high possibility of catalyst deterioration. To prevent the deterioration, it is possible to lower the catalyst particle ratio in the former stage and to increase the catalyst particle ratio in the latter stage.

Differences in reaction conversions among the respective reaction tubes may affect the average conversion and yield of the entire reactor. Therefore, it is preferable that the dilution rate is set so that the same conversion is obtained in the respective reaction tubes even when dilution ratios are changed.

The present invention is suitably applied to a multitube reactor for oxidizing propylene or isobutylene with a molecular oxygen-containing gas or to a multitube reactor in which (meth)acrolein is oxidized with a molecular oxygen-containing gas to yield (meth)acrylic acid. A catalyst used in oxidation of propylene is preferably a multicomponent mixed metal oxide, mainly an Mo—Bi mixed metal oxide. A catalyst used in oxidation of acrolein to yield acrylic acid is preferably an Sb—Mo mixed oxide.

Propylene or isobutylene is typically oxidized in 2 stages and hence different catalysts may be packed inside 2 multitube reactors to carry out a reaction. Alternatively, the present invention can also be applied to the case of yielding (meth)acrylic acid in a single reactor with the shell of the reactor divided into 2 or more chambers by intermediate tube plates as shown in FIG. 5 and with the chambers packed with different catalysts.

In a multitube reactor for oxidizing propylene or isobutylene with a molecular oxygen-containing gas, when the reactor shown in FIG. 1 is adopted and the raw material gas Rg enters from 4a and is discharged from 4b, the concentration of the target product (meth) acrolein is high in the vicinity of the shell outlet 5b. In addition, the temperature of the raw material gas increases because the raw material gas is heated by the heat of reaction. Therefore, in this case, a heat exchanger is additionally provided in the course of the raw material gas Rg following 4b of the shell shown in FIG. 1, to thereby sufficiently cool the reaction gas to prevent (meth)acrolein from causing an autooxidation reaction.

In the case where the reactor shown in FIG. 5 is adopted, when the raw material gas Rg enters from 4a and is discharged from 4b, the concentration of the target product (meth)acrolein is high in the vicinity of the catalyst layer outlet 9 in the former stage. In addition, the temperature of the raw material gas increases because the gas is heated by the heat of reaction.

When a catalyst is packed only into 5a-6a-6b-6a-9, no reaction is carried out in the catalyst layer outlet portion (between 9 and 5b) in the latter stage of the reaction tubes 1a, 1b, and 1c. The raw material gas is cooled by the heat media Hm1 and Hm2 flowing through flow paths to the shell in order to prevent (meth)acrolein from causing an autooxidation reaction. In this case, the gas outlet portion (between 9 and 5b) of each of the reaction tubes 1a, 1b, and 1c is packed with no catalyst or with an inert substance without reaction activity. However, the latter is preferably packed for improving heat transfer characteristics.

In addition, in FIG. 5, in the case where the catalyst layer (5a-6a-6b-6a-9) in the former stage on the inlet side of the raw material gas Rg and the catalyst layer (9-6a'-6b'-6a'-5b) in the latter stage on the outlet side of the gas are packed with different catalysts to obtain (meth)acrolein and (meth)acrylic acid from propylene and isobutylene, the temperature of the catalyst layer in the former stage is higher than that of the catalyst layer in the latter stage. Therefore, no reaction is carried out around the catalyst layer outlet (6a-9) in the former stage and the catalyst layer inlet (9-6a') in the latter stage because a position around them has a high temperature. The raw material gas is cooled by the heat medium flowing through a flow path to the shell side in order to prevent (meth)acrolein from causing an autooxidation reaction.

In this case, a portion into which no catalyst is packed is provided among 6a-9-6a' of the reaction tubes 1a, 1b, and 1c to serve as a cavity. Alternatively, an inert substance without reaction activity is packed among 6a-9-6a' of the reaction tubes 1a, 1b, and 1c. However, the latter is preferably packed for improving heat transfer characteristics.

A vapor phase catalytic oxidation reaction involves: mixing propylene or isobutylene as a raw material with molecular oxygen and an inert gas such as nitrogen, carbon dioxide, or water vapor to prepare a raw material gas; and reacting the raw material gas in the presence of a solid catalyst to yield acrolein and acrylic acid or methacrolein and methacrylic acid. Any conventionally known catalyst is available for the catalyst. According to the present invention, it is also possible to yield acrylic acid by subjecting propane to vapor phase oxidation by using a Mo—V—Te mixed oxide catalyst, Mo—V—Sb mixed oxide catalyst, or the like.

The composition of a former stage reaction catalyst (for a reaction converting an olefin into an unsaturated aldehyde or an unsaturated acid) that can be preferably used in the present invention is represented by the following general formula (I).

$$Mo_aW_bBi_cFe_dA_eB_fC_gD_hE_iO_j \quad (I)$$

(wherein, Mo represents molybdenum; W represents tungsten; Bi represents bismuth; Fe represents iron; A represents at least one type of element chosen from nickel and cobalt; B represents at least one type of element selected from the group consisting of sodium, potassium, rubidium, cesium, and thallium; C represents at least one type of element selected from alkaline earth metals; D represents at least one type of element selected from the group consisting of phosphorus, tellurium, antimony, tin, cerium, lead, niobium, manganese, arsenic, boron, and zinc; E represents at least one type of element selected from the group consisting of silicon, aluminum, titanium, and zirconium; o represents oxygen; a, b, c, d, e, f, g, h, i, and j represent atomic ratios of Mo, W, Bi, Fe, A, B, C, D, E, and O respectively; and if a=12, $0 \leq b \leq 10$, $0 < c \leq 10$, $0 < d \leq 10$, $2 \leq e \leq 15$, $0 < f \leq 10$, $0 \leq g \leq 10$, $0 \leq h \leq 4$, and $0 \leq i \leq 30$; and j is a value determined from oxidation states of the respective elements.)

In the multitube reactor of the present invention, c, d, and f in the above general formula (I) preferably satisfy $0.1 \leq c \leq 10$, $0.1 \leq d \leq 10$, and $0.001 \leq f \leq 10$.

Further, the composition of a latter stage reaction catalyst (for a reaction converting an olefin into an unsaturated aldehyde or an unsaturated acid) that can be preferably used in the present invention is represented by the following general formula (II).

$$Sb_kMo_l(V/Nb)_mX_nY_pSi_qO_r \quad (II)$$

(wherein, Sb represents antimony; Mo represents molybdenum; V represents vanadium; Nb represents niobium; X represents at least one type of element selected from the group consisting of iron (Fe), cobalt (Co), nickel (Ni), and bismuth (Bi) ; Y represents at least one type of element chosen from copper (Cu) and/or tungsten (W); Si represents silicon; O represents oxygen; (V/Nb) represents V and/or Nb; k, l, m, n, p, q, and r represent atomic ratios of Sb, Mo, (V/Nb), X, Y, Si, and O respectively; and $1 \leq k \leq 100$, $1 \leq l \leq 100$, $0.1 \leq m \leq 50$, $1 \leq n \leq 100$, $0.1 \leq p \leq 50$, $1 \leq q \leq 100$; and r is a value determined from oxidation states of the respective elements.) In the multitube reactor of the present invention, k, l, m, n, p, and q in the above general formula (II) preferably satisfy $10 \leq k \leq 100$, $1 \leq l \leq 50$, $1 < m \leq 20$, $10 \leq n \leq 100$, $1 \leq p \leq 20$, and $10 \leq q \leq 100$.

The shape of and molding method for a catalyst used are described. A catalyst used in the multitube reactor of the present invention may be a molded catalyst molded through extrusion molding or tablet compression or may be a catalyst prepared by supporting a mixed oxide composed of a catalyst component on an inert support such as silicon carbide, alumina, zirconium oxide, or titanium oxide.

The shape of a catalyst used in the present invention is not particularly limited and may be spherical, cylindrical, ring-shaped, amorphous, or the like.

In particular, the use of a ring-shaped catalyst has an effect of preventing heat storage in hot spot portions.

A catalyst packed into a reaction tube inlet may have the same or different composition and shape with a catalyst packed into an upper portion of the reaction tube.

An inert substance used for catalyst dilution in the present reaction is not limited as long as the inert substance is stable under the conditions of the present reaction and has no reactivity with a raw material substance and a product. Specific examples of the inert substance include those typically used as catalyst supports such as alumina, silicon carbide, silica, zirconium oxide, and titanium oxide. In addition, as in the case of the catalyst, the shape of the inert substance is not limited and may be spherical, cylindrical, ring-shaped, amorphous, or the like. The size of the inert substance may be set in consideration of the diameter of a reaction tube and differential pressure in a reaction tube.

In the case where a multitube reactor is used and a plurality of reaction zones are provided by dividing the inside of each reaction tube in its axial direction, the number of reaction zones may be appropriately selected in such a manner providing the maximum effect of the reaction zones. However, an excessively large number of reaction zones requires much effort for catalyst packing. Therefore, an industrially desirable number of reaction zones is about 2 to 5.

In addition, the length of a reaction zone may be appropriately selected in such a manner that the maximum effect of the present invention is exerted because the most suitable value of the length is determined by the catalyst type, the number of reaction zones, the reaction conditions, and the like. The length of each reaction zone is typically 10 to 80%, preferably 20 to 70%, of the total length.

According to the present invention, the catalytic activity of a catalyst packed into a plurality of reaction zones is controlled by altering mixing with an inert substance, a shape of the catalyst, a composition of the catalyst, and a burning temperature upon catalyst preparation, and, if the catalyst is a supported catalyst, the amount of a catalyst active ingredient supported.

<First Vapor Phase Catalytic Oxidation Method>

The inventors of the present invention have devoted themselves to research and have confirmed that the above-mentioned problems such as yield reduction and reduced catalyst life arise when catalyst layer peak temperature sites, which are high temperature portions of the catalyst layers, are located at portions where a heat medium does not flow at all or hardly flows due to baffles. The inventors of the present invention have found out that the following methods can provide a vapor phase catalytic oxidation method solving the above-mentioned problems and have completed the present invention.

That is, the first vapor phase catalytic oxidation method is a vapor phase catalytic oxidation method: using a fixed bed multitube heat-exchanger type reactor having a plurality of reaction tubes and baffles for changing a flow path of a heat medium; circulating the heat medium through the outside of the of the reaction tubes; and feeding a raw material gas into the reaction tubes packed with a catalyst, to thereby obtain a reaction product gas, wherein the method comprises, catalyst packing specifications in the reaction tubes are determined so that catalyst layer peak temperature sites of the reaction tubes are not located at the connecting sites between the baffles and the reaction tubes.

Hereinafter, the first vapor phase catalytic oxidation method will be described in detail.

The first vapor phase catalytic oxidation method involves vapor phase catalytic oxidation using a fixed bed multitube heat-exchanger type reactor having a plurality of reaction tubes and baffles for changing a flow path of a heat medium. That is,.a reaction product gas is formed in the reactor by circulating the heat medium through the outside of the reaction tubes, and feeding a raw material gas into the reaction tubes packed with a catalyst.

In the first vapor phase catalytic oxidation method, the heat medium is preferably used for absorbing heat of reaction generated from the reaction tubes. Any material can be used for the heat medium as long as the material has a function of absorbing the heat of reaction generated from the reaction tubes. Examples of the heat medium include: organic heating media such as partially-hydrogenated triphenyl; and inorganic molten salts such as alkali metal (such as sodium and potassium) nitrate or nitrite, so-called niter.

Further, in the first vapor phase catalytic oxidation method, the raw material gas or the catalyst for the reaction can be appropriately selected in accordance with a desired type of the reaction product gas.

Through the first vapor phase catalytic oxidation reaction method, (meth) acrolein or (meth) acrylic acid can be produced from propane, propylene, or isobutylene in the presence of a mixed oxide catalyst using molecular oxygen or a molecular oxygen-containing gas, for example. To be specific, (meth)acrylic acid can be produced by: oxidizing propylene or isobutylene in the presence of a Mo—Bi mixed oxide catalyst to mainly produce (meth)acrolein (former stage reaction); and oxidizing the (meth) acrolein produced in the former stage reaction in the presence of a Mo—V mixed oxide catalyst. Further, acrylic acid can also be produced through vapor phase oxidation of propane using a Mo—V—Te mixed oxide catalyst or a Mo—V—Sb mixed oxide catalyst.

The following production systems are effective especially for commercialization in production of the (meth)acrolein or (meth)acrylic acid through the first vapor phase catalytic oxidation method. Hereinafter, the production systems will be described using propylene as an example.

1) One-Pass System

The one-pass system involves: mixing and feeding propylene, air, and steam to mainly produce acrolein and acrylic acid (former stage reaction); feeding the gas obtained in the former stage reaction to a latter stage reaction without separating products; and feeding air and steam required for the latter stage reaction in addition to the gas obtained in the former stage reaction.

2) Unreacted Propylene Recycle System

The unreacted propylene recycle system for recycling a part of the unreacted propylene involves: guiding a reaction product gas containing acrylic acid obtained through the latter stage reaction to an acrylic acid collecting device; collecting the acrylic acid in an aqueous solution; separating a part of a waste gas containing the unreacted propylene from the collecting device; and feeding the waste gas to the former stage reaction again.

3) Combustion Waste Gas Recycle System

The combustion waste gas recycle system involves: guiding the reaction product gas containing acrylic acid obtained through the latter stage reaction to the acrylic acid collecting device; collecting the acrylic acid in an aqueous solution; catalytically combusting and oxidizing all waste gas from the collecting device to convert the unreacted propylene or the like in the waste gas to mainly carbon dioxide and water; and feeding a part of the obtained combustion waste gas to the former stage reaction again.

The first vapor phase catalytic oxidation method can be carried out using any one of the above-mentioned systems for commercial production, and the production system is not particularly limited.

Further, a Mo—Bi mixed oxide catalyst represented by the general formula (I) is preferably used in the above-mentioned multitube reactor of the present invention as a catalyst used in the former stage reaction for obtaining the above-mentioned olefin from unsaturated aldehyde or unsaturated acid.

Further, a Mo—V mixed oxide catalyst represented by the general formula is preferably used as a catalyst used in the latter stage reaction for obtaining the above-mentioned olefin from unsaturated aldehyde or unsaturated acid.

$$Mo_aV_bW_cCu_dX_eY_fO_g$$

(wherein, Mo represents molybdenum; V represents vanadium; W represents tungsten; Cu represents copper; X represents at least one type of element selected from the group consisting of Mg, Ca, Sr, and Ba; Y represents at least one type of element selected from the group consisting of Ti, Zr, Ce, Cr, Mn, Fe, Co, Ni, Zn, Nb, Sn, Sb, Pb, and Bi; O represents oxygen; a, b, c, d, e, f, and g represent atomic ratios of Mo, V, W, Cu, X, Y, and O respectively; if a=12, $2 \leq b \leq 14$, $0 \leq c \leq 12$, $0 < d \leq 6$, $0 \leq e \leq 3$, and $0 \leq f \leq 3$; and g is a value determined from oxidation states of the respective elements.)

The reaction tubes used in the first vapor phase catalytic oxidation method are packed with the catalyst and an inert substance for dilution of the catalyst (hereinafter, may be referred to as "diluent") as the need arises.

Further, packing specifications for packing the catalyst in the reaction tubes may be set by considering all the factors involved such as a type of the catalyst, an amount of the catalyst, a form of the catalyst (shape, size), a method for diluting the catalyst (a type of the diluent, an amount of the diluent), and lengths of reaction zones. The lengths of reaction zones are adjusted depending on a form of the catalyst, an amount of the catalyst, and usage of the diluent with.

The form of the catalyst and a method for molding the catalyst employed in the present invention are determined in the same manner as for the above-mentioned multitube reactor of the present invention. Further, the diluent is determined in the same manner as for the inert substance that employed for the above-mentioned multitube reactor of the present invention.

A mixing ratio of the catalyst and the diluent is not particularly limited, but when the mixing ratio is extremely large or small, the mixing ratio may be adjusted so that the catalyst and the diluent are uniformly mixed.

Further, the packing specifications for packing the catalyst may differ according to layers of reaction zones of one reaction tube. For example, packing specifications for packing the catalyst packed in an upper portion of a reaction tube may differ from the packing specifications for packing the catalyst packed in a lower portion of the reaction tube. Generally, the preferred number of reaction zones is up to 2 to 3 in one reaction tube.

Further, the catalyst is preferably packed so that the catalytic activity increases from an inlet portion of the reaction tubes where a raw material gas is introduced toward an outlet portion of the reaction tubes.

In the first vapor phase catalytic oxidation method, catalyst layer peak temperature sites of the reaction tubes are not located at connecting sites between the baffles and the reaction tubes.

Here, the catalyst layer peak temperature refers to the highest temperature of the catalyst layer measured during a reaction. The catalyst layer peak temperature sites refer to: a portion of the catalyst layer having the highest temperature when the catalyst is packed in a reaction tube in a single layer; and to respective portions of the catalyst layers having the highest temperature in respective reaction zones when the catalyst is packed in several reaction zones.

The catalyst layer peak temperature is determined as follows.

The temperatures of the respective portions of the catalyst layer are determined by packing the catalyst after inserting a multi-point thermocouple to the reaction tube and measuring the temperatures of the respective portions of the catalyst layer. Note that, the number of measurement points of the multi-point thermocouple is generally 5 to 100 points, preferably 7 to 50 points, and more preferably 10 to 30 points. Alternatively, the temperature is determined by packing the catalyst after inserting a well in the reaction tubes and measuring the temperature while moving thermocouple inside the well. The catalyst layer peak temperature indicates portions of the catalyst layer having the highest temperatures in the respective reaction zones when using a movable thermocouple and portions of measurement points having the highest temperatures in the respective reaction zones when using the multi-point thermocouple.

In the first vapor phase catalytic oxidation method, the connecting sites between the baffles and the reaction tubes, more specifically, refer to sites where the baffles and the reaction tubes are fixed to each other through welding, a frange, or the like or where the baffles exist across the reaction tubes if they are not fixed to each other.

Further, in the first vapor phase catalytic oxidation method, the catalyst packing specifications in the reaction tubes are set so that the catalyst layer peak temperature sites of the reaction tubes are not located at the connecting sites between the baffles and the reaction tubes That is, the packing specifications are changed for the reaction tubes having the catalyst layer peak temperature sites of the reaction tubes located at the connecting sites between the baffles and the reaction tubes. The catalyst packing specifications can be changed in view of the respective factors such as a type of the catalyst, an amount of the catalyst, a form of the catalyst (shape, size), a method for diluting the catalyst (a type of the diluent, an amount of the diluent), and lengths of reaction zones.

In the first vapor phase catalytic oxidation method, the catalyst is preferably packed so that the catalyst layer peak temperature sites inside the reaction tubes are not located in the range of ±100% of baffle thickness from the center of the thickness of a baffle, where the direction along a surface of one side of the baffle is referred to as a + direction and the direction along a surface of the other side of the baffle is referred to as a —direction to the center of the tickness of the baffle. Here, the thickness of the baffles generally used is about 5 to 50 mm.

In the first vapor phase catalytic oxidation method, the catalyst packing specifications are more preferably changed by providing in one reaction tube at least two catalyst layers with different catalyst packing specifications. The catalyst layer peak temperature sites can be transferred longitudinally along the reaction tube by particularly changing the lengths of the reaction zones for the reaction tube having a plurality of reaction zones.

Further, In the first vapor phase catalytic oxidation method, the catalyst packing specifications are preferably set to minimize the heat of reaction at the connecting sites between the baffles and the reaction tubes by, for example, forming an inert layer composed of the diluent alone or increasing an amount of the diluent at the connecting sites.

Further, in the first vapor phase catalytic oxidation method, a plurality of reaction tubes with different catalyst packing specifications may be formed inside one reactor as long as the catalyst layer peak temperature sites of the reaction tubes are not located at the connecting sites between the baffles and the reaction tubes.

FIG. 7 shows a first embodiment mode of a fixed bed multitube heat-exchanger type reactor employed in the first vapor phase catalytic oxidation method.

FIG. 7 shows: a reactor 1; a raw material gas introducing port (for a downflow case) or a reaction product gas discharging port (for an upflow case) 2; a reaction product gas discharging port (for a downflow case) or a raw material gas introducing port (for an upflow case) 3; a reaction tube (catalyst packed inside) 4; an upper tube plate 5; a lower tube plate 6; baffles 7, 8, and 9; a heat medium outlet nozzle 10; a heat medium inlet nozzle 11; a heat medium inlet line for reaction temperature adjustment 13; and a heat medium overflow line 14.

Note that the fixed bed multitube heat-exchanger type reactor shown in FIG. 7 is a structure employed when allowing the heat medium to flow in an upflow direction, but the heat medium can be obviously flown in a downflow direction as well in the first vapor phase catalytic oxidation method.

The raw material gas is mixed with air and/or a diluent gas, a recycle gas, or the like, introduced from the raw material gas introducing port (2 or 3) to the reactor (1), and fed to the reaction tube (4) packed with the catalyst. The reaction product gas produced by oxidation through a catalytic oxidation reaction inside the reaction tube and an unreacted gas are discharged from the reaction product gas discharging port (3 or 2).

The heat medium is introduced from the heat medium inlet nozzle (11) to a shell by a pump (12), passed through inside the shell while removing the heat of reaction generated inside the reaction tube, discharged from the heat medium outlet nozzle (10), and circulated by the pump. The heat medium temperature is controlled by introducing the heat medium from the heat medium inlet line for reaction temperature adjustment (13), and the amount of the heat medium introduced from the heat medium inlet line for reaction temperature adjustment (13) is discharged from the heat medium overflow line (14).

A structure of the baffles of the fixed bed multitube heat-exchanger type reactor employed in the first vapor phase catalytic oxidation method is not particularly limited. Any type of the fixed bed multitube heat-exchanger type reactor can be used including: a double segment-type baffle type shown in FIG. 8; a disc and doughnut baffle type shown in FIG. 9; and a multi baffle type shown in FIG. 10. Note that, in FIGS. 8 to 10, shapes of the baffles and a flow of the heat medium are described.

FIG. 11 is a schematic diagram illustrating that the heat medium does not flow through the connecting sites between the baffles and the reaction tubes fixed through welding, franges, or the like in the fixed bed multitube heat-exchanger type reactor. Further, FIG. 12 is a schematic diagram illustrating that the amount of the heat medium flowing through the connecting sites between the baffles and the reaction tubes are limited if the baffles exist across the reaction tubes, if not fixed to the reaction tubes. In FIGS. 11 and 12, reference numerals 15 and 16 represent a reaction tube and a baffle, respectively. Further, reference numerals 17 and 18 represent a flow of the heat medium.

<Second Vapor Phase Catalytic Oxidation Method>

The inventors of the present invention have found that the process gas temperature in the vicinity of the product discharging port of the reactor can be reduced to prevent an autooxidation reaction, even under conditions of high product concentration by diluting the catalyst with the inert substance for reducing the catalyst layer peak temperature inside the reaction tubes and employing a countercurrent-type heat medium circulation method, to thereby complete the present invention.

That is, the gist of the second vapor phase catalytic oxidation method is as described below.

The second vapor phase catalytic oxidation method is a method of obtaining (meth) acrolein and/or (meth) acrylic acid by oxidizing propylene, propane, isobutylene, and/or (meth)acrolein through vapor phase catalytic oxidation with a molecular oxygen-containing gas using a multitube reactor having: a cylindrical shell having a raw material feed port and a product discharging port; a plurality of ring-shaped tubes arranged on an outer periphery of the cylindrical shell for introducing or discharging a heat medium into or from the cylindrical shell; a circulating device connecting the plurality of ring-shaped tubes with each other; a plurality of reaction tubes restrained by a plurality of tube plates of the reactor and containing a catalyst; and a plurality of baffles arranged in a longitudinal direction of the reaction tubes for changing a direction of the heat medium introduced into the shell, wherein the method comprises: packing a Mo—Bi catalyst and/or Sb—Mo catalyst in the reaction tubes so that activity increases from a process gas inlet to a process gas outlet of the reaction tubes; and allowing the heat medium and the process gas to flow in a countercurrent.

Hereinafter, the second vapor phase catalytic oxidation method will be described in detail.

A multitube reactor is generally used when heat of reaction is extremely large as in an oxidation reaction and when productivity of the reactor must be improved by protecting a catalyst through rigorous control of catalyst reaction temperature and maintaining high catalyst performance.

Recently, production of acrylic acid from propylene or propane, or production of methacrylic acid from isobutylene (hereinafter, collectively referred to as production of (meth) acrylic acid) has significantly increased with increasing demand. Many plants have been constructed worldwide, and a production scale per a plant has increased to 100,000 tons or more per year. Increase of a production scale of a plant requires increase of production per oxidation reactor. As a result, a load on a vapor phase catalytic oxidation reactor for propylene or isobutylene has increased. Along with the load increase, the multitube reactor has been required to provide higher performance in terms of increase in an amount of heat removal, and development of the multitube reactor has become important.

The second vapor phase catalytic oxidation is a vapor phase catalytic oxidation method comprising oxidizing an oxidizable reactant through vapor phase catalytic oxidation with a molecular oxygen-containing gas using a multitube reactor having: a cylindrical shell having a raw material feed port and a product discharging port; a plurality of ring-shaped tubes arranged on an outer periphery of the cylindrical shell for introducing or discharging a heat medium into or from the cylindrical shell; a circulating device for connecting the plurality of ring-shaped tubes with each other; a plurality of reaction tubes restrained by a plurality of tube plates of the reactor and containing a catalyst; and a plurality of baffles arranging in a longitudinal direction for changing a direction of the heat medium introduced into the shell, the method being characterized by comprising: packing a Mo—Bi catalyst and/or Sb—Mo catalyst in the reaction tubes so that activity increases from a process gas inlet to a process gas outlet of the reaction tubes; and allowing the heat medium and the process gas to flow in a countercurrent.

In particular, the second vapor phase catalytic oxidation method is a vapor phase catalytic oxidation method of obtaining (meth)acrolein and/or (meth)acrylic acid through vapor phase catalytic oxidation of propylene, propane, or isobutylene, and/or (meth)acrolein as an oxidizable reactant with a molecular oxygen-containing gas.

In the second vapor phase catalytic oxidation method, the term "process gas" refers to a gas involved in a vapor phase catalytic oxidation reaction including an oxidizable reactant as a raw material gas, a molecular oxygen-containing gas, and obtained products.

Hereinafter, one embodiment mode of the second vapor phase catalytic oxidation method will be described with reference to FIG. 1. The reaction tubes 1b and 1c are arranged in the shell 2 of the multitube reactor, fixed onto the tube plates 5a and 5b. A raw material feed port as an inlet of a raw material gas or a product discharging port as an outlet of the products is represented by reference numeral 4a or 4b. As long as the process gas and the heat medium are in a countercurrent, a flow direction of the process gas is not limited. In FIG. 1, the flow direction of the heat medium inside the shell is indicated by arrows as an upflow, and thus reference numeral 4a represents the raw material feed port. The ring-shaped tube 3a for introducing the heat medium is provided on the outer periphery of the shell. The, heat medium pressurized with the circulating pump 7 of the heat medium flows upward inside the shell from the ring-shaped tube 3a. The flow direction of the heat medium is changed by plurally and alternately arranging the perforated baffle 6a having an opening portion in the vicinity of the center of the shell and the perforated baffle 6b provided to have an opening portion between the baffle and the outer periphery of the shell. The heat medium is then returned from the ring-shaped tube 3b to the circulating pump. A part of the heat medium absorbing the heat of reaction flows toward the discharging tube provided in upper portion of the circulating pump 7, is cooled with the heat exchanger (not shown), and is introduced into the reactor again from the heat medium feed line 8a. The heat medium temperature is adjusted by adjusting temperature or a flow rate of a returning heat medium introduced from the heat medium feed line 8a to control thermometer 14.

The heat medium temperature is adjusted so that a temperature difference of the heat medium between the heat medium feed line 8a and the heat medium draw line 8b is 1° C. to 10° C., preferably 2° C. to 6° C., though depending on the performance of the catalyst used.

A flow-rectifying plate (not shown) is preferably provided in a body plate portion inside the ring-shaped tubes 3a and 3b for minimizing a flow rate distribution of the heat medium in a circumferential direction. A porous plate or a plate provided with slits is used as the flow-rectifying plate, and the flow of heat medium is adjusted by changing an opening area of the porous plate or slit intervals so that the heat medium flows at the same flow rate from the entire circumference. The temperature inside the ring-shaped tubes (3a, preferably also 3b) can be monitored by providing the plurality of thermometers 15.

The number of the baffles provided inside the shell is not particularly limited, but three baffles (2 baffles of 6a type and 1 baffle of 6b type) are preferably provided as usual. The baffles prevent an upflow of the heat medium, changes the flow of the heat medium to a lateral direction with respect to an axial direction of the reaction tubes. The heat medium converges from an outer peripheral portion to a central portion of the shell, changes direction in the opening portion of the baffle 6a, flows to the outer peripheral portion of the shell, and reaches the outer cylinder of the shell. The heat medium changes direction again on an outer periphery of the baffle 6b, converges to the central portion, flows upward through the opening portion of the baffle 6a, flows along the upper tube plate 5a toward the outer periphery of the shell, and flows through the ring-shaped tube 3b to circulate to the pump.

Thermometers 11 are inserted to the reaction tubes arranged inside the reactor and signals are transmitted to the outside of the reactor, to thereby record temperature distributions of the catalyst layers in an axial direction of the reactor. Multiple thermometers are inserted to the reaction tubes, and one thermometer measures temperatures of 5 to 20 points in an axial direction of the tube.

The reaction tubes are classified into two types depending on their placements in relation to opening portions of the three baffles, that is, on flow directions of the heat medium.

The reaction tube 1b is restrained by the three baffles 6a, 6b, and 6c, and most of the reaction tubes are arranged in this region. The flow direction of the heat medium in the entire region of the reaction tube 1b is substantially at a right angle with an axial direction of the reaction tubes. The reaction tube 1c is in the vicinity of the outer periphery of the shell, is not restrained by the baffle 6b, and is provided in the outer peripheral portion of the baffle 6b. The central portion of the reaction tube 1c is in a region where a flow direction of the heat medium changes, in this region, that is, in the central portion of the reaction tube 1c, the heat medium flows in parallel with an axial direction of the reaction tubes.

FIG. 4 shows a view of the reactor of FIG. 1 seen from above. Not only the flow of the heat medium becomes parallel with the axial direction of the reaction tubes but also the flow rate of the heat medium becomes extremely small to provide extremely poor heat transfer efficiency in the region where the heat medium converges at the opening portion of the baffle 6a, that is, at the center of the shell. Thus, the reaction tubes are not provided in the central portion of the region in the second vapor phase catalytic oxidation reaction.

The baffles used in the second vapor phase catalytic oxidation method includes: the baffle 6a having an opening portion in the vicinity of the central portion of the shell; and the baffle 6b having an opening between the outer peripheral portion of the baffle 6b and the outer cylinder of the shell. The heat medium changes direction at the respective opening portions, preventing a by-pass flow of the heat medium and enabling a change in flow rate. Segment-type noncircular baffles shown in FIG. 2 or disc-type baffles shown in FIG. 3 can be applied as long as the baffles are arranged as described. The relationship between the flow direction of the heat medium and the axial direction of the reaction tubes does not change with both types of baffles.

The disc-type baffles are particularly used often as general baffles. An opening area in the central portion of the baffle 6a is preferably 5 to 50%, more preferably 10 to 30% of a sectional area of the shell. The opening area between the baffle 6b and the shell body plate 2 is preferably 5 to 50%, more preferably 10 to 30% of a sectional area of the shell. A too small opening ratio of the baffles (6a and 6b) provides a long flow path of the heat medium, increasing a pressure loss between the ring-shaped tubes (3a and 3b) and requiring high power for the heat medium circulating pump 7. A too large opening ratio of the baffles increases the number of the reaction tubes (1c) Most of the baffles are arranged at equal spacings (spacing between baffles 6a and 6b, and spacing between baffle 6a and each of tube plates 5a and 5b), but the baffles need not to be arranged at equal spacings. It is preferable that a required flow rate of the heat medium determined by heat of oxidation reaction generated inside the reaction tubes is ensured and a pressure loss of the heat medium remains low. Hot spot positions in a temperature distribution in the reaction tubes and the baffle positions must not be the same from the ring-shaped tube 3a at the inlet of the heat medium. This is because the flow rate of the heat medium decreases in the vicinity of baffle surface, providing a small heat transfer coefficient. Thus, hot spot temperature further increases when the baffle positions overlap the hot spot positions.

Studies are preferably conducted for preventing the hot spot position from being located in the same position as the baffles, through experiments with small scale devices (such as bench facility and a pilot facility) or computer simulation carried out in advance.

The types and ratios of raw material gas components and importance of uniform packing of the catalyst are the same as those for the above-mentioned multitube reactor of the present invention. Note that, in the second vapor phase catalytic oxidation method, concentration of propylene, propane, or isobutylene in the raw material gas is preferably 6 to 10 mol %.

The arrangement of the catalyst in layers inside the reaction tubes, which increases the activity from the raw material gas inlet to the outlet, can suppress hot spot formation and heat storage of the hot spot portions. Thus, the reaction can be carried out safely and efficiently, to thereby attain improvements on productivity without reducing the catalyst life.

Various methods for changing the catalytic activity inside the reaction tubes can be applied to catalyst packing to the reaction tubes of the multitube reactor according to the second vapor phase catalytic oxidation method. Examples thereof include: a method of using catalysts having different catalytic activities by adjusting catalyst compositions; and a method of adjusting the activities by mixing catalyst particles with inert substance particles and diluting the catalyst. To be specific, a catalyst having a high ratio of the inert substance particles and a catalyst having a low ratio of the inert substance particles are packed in the raw material gas inlet portion of the reaction tubes and the outlet portion of the reaction tubes, respectively. The ratio of the inert substance particles used differs depending on the catalyst. The ratio of the inert substance particles used in a first stage is often 0.3 to 0.7. The ratio of the inert substance particles used in a second stage is suitably 0.5 to 1.0. Two to five stages are adopted in the change of activity and the dilution of the catalyst generally.

A dilution degree of the catalyst packed in the reaction tubes need not be the same for all the reaction tubes. For example, a portion in the vicinity of the reaction tube center within the reaction tube 1b has high hot spot temperature, and thus has a high possibility of catalyst deterioration. To prevent catalyst deterioration, the reaction tube in such a portion can have a smaller ratio of the inert substance in the first stage compared to those of the reaction tubes in other portions, and on the other hand, can have a larger ratio of the catalyst in the second stage compared to those of the reaction tubes in other portions. Different reaction conversions of the respective reaction tubes affect the average conversion or yield of the entire reactor. Thus, even when the dilution degree is changed, it is preferable to set the respective reaction tubes to obtain the same conversions.

The type and shape of the inert substance used in the second vapor phase catalytic oxidation reaction method are the same as those for the above-mentioned multitube reactor of the present invention.

The raw material gas flowing through the reaction tubes is heated while first flowing through catalyst layers packed in the raw material gas inlet portions of the reaction tubes and having a low catalytic activity, and reaches a reaction starting temperature. The raw material (propylene or isobutylene) is oxidized through an oxidation reaction by a catalyst included in succeeding layers in the reaction tubes, and is heated to higher temperature by the heat of oxidation reaction. The reaction weight is most in the catalyst layers in the vicinity of the raw material gas inlet. The heat of reaction generated increases the temperature of the raw material gas when the heat of reaction is greater than the heat removal by the heat medium generally, thereby forming the hot spots. The hot spots, though depending on catalytic activity adjustment, often form at positions from the raw material gas inlet of the reaction tubes to 10 to 80% of the entire length of the reaction tubes. For example, the hot spot form at positions 0.3 to 3.2 m from the raw material gas inlet of the reaction tubes that are 3 to 4 m long.

The effect of the generated heat of reaction on the catalyst, the heat medium temperature in acrolein production through an oxidation reaction of propylene with a molecular oxygen-containing gas, the allowable maximum temperature of the hot spots, the type of the heat medium used in the second vapor phase catalytic oxidation reaction, and the effect of a fluid state of the heat medium on heat removal efficiency are the same as those of the above-mentioned multitube reactor of the present invention.

Inner diameters of the reaction tubes significantly affecting a gas linear velocity are very important because: inside of the reaction tubes containing an oxidation catalyst inside the oxidation reactor is in a vapor phase; the gas linear velocity is limited by resistance of the catalyst; and the heat transfer coefficient inside the reaction tubes are very small, the heat transfer becoming rate determining.

The inner diameters of the reaction tubes of the multitube reactor according to the second vapor phase catalytic oxidation reaction method depend on the amount of the heat of reaction and a particle size of the catalyst inside the reaction tubes, but the inner diameter is preferably 10 to 50 mm, more preferably 20 to 30 mm. Too small inner diameters of the reaction tubes decrease the amount of the catalyst packed and increase the number of reaction tubes with respect to the necessary amount of the catalyst, thereby requiring a large reactor. On the other hand, too large inner diameters of the reaction tubes provide a small reaction tube surface area with respect to the necessary amount of the catalyst, thereby reducing a heat transfer area for removal of the heat of reaction.

The second vapor phase catalytic oxidation method is suitably applied to: a vapor phase catalytic oxidation reaction for obtaining (meth)acrolein by oxidizing propylene, propane, or isobutylene with a molecular oxygen-containing gas; and a vapor phase catalytic oxidation reaction for obtaining (meth)acrylic acid by oxidizing (meth)acrolein with a molecular oxygen-containing gas. A Mo—Bi multi-component mixed metal oxide is used as the catalyst for the oxidation of propylene, propane, and isobutylene, and a Sb—Mo multi-component mixed metal oxide is used as the catalyst for the oxidation of acrolein to produce acrylic acid.

Note that, the Mo—Bi catalyst preferably used in the second vapor phase catalytic oxidation method is the same as that represented by the general formula (I) in the above-mentioned multitube reactor of the present invention. Note that, the Mo—Bi catalyst used in the second vapor phase catalytic oxidation method is preferably produced through methods disclosed in JP 06-013096 B and the like, for example. Further, the Sb—Mo catalyst is preferably produced through methods disclosed in JP 06-38918 B and the like, for example.

The Mo—Bi catalyst is produced following general production methods except that a mixed carbonate salt of a C component and Bi is prepared in advance as a Bi source compound, for example. The preparation of the mixed carbonate salt of a C component and B in advance involves, for example: mixing predetermined amounts of respective aqueous nitrate solutions of Bi and the C component; adding the nitrate solutions dropwise to an aqueous solution of ammonium carbonate or ammonium bicarbonate while mixing the whole; and washing the obtained precipitate and drying the precipitate if necessary.

The production of the Mo—Bi catalyst generally includes an integration step of performing integration of source compounds of the respective elements in an aqueous system and a heating step. Here, the term "integration of source compounds of the respective elements in an aqueous system" means temporarily or gradually integrating aqueous solutions or aqueous dispersions of the respective compounds. Here, the term "source compounds of the respective elements" does not mean compounds of the respective elements alone, but includes compounds collectively containing multiple elements (such as ammonium phosphomolybdate for Mo and P). Further, the term "integration" does not mean integration of the source compounds of the respective elements alone, but also includes integration with support materials such as alumina, silica-alumina, and refractory oxides, which may be used if necessary.

On the other hand, "heating" is carried out for the purposes including: formation of separate oxides and/or mixed oxides of the source compounds of the respective elements; and/or formation of oxides and/or mixed compounds of the mixed oxides obtained through integration; and/or heat treatment of the final mixed oxide products. Further, the heating need not be applied to primarily integration products of the source compounds of the respective elements, and the heating is not necessarily limited to once.

Thus, in the second vapor phase catalytic oxidation method, the term "heating" includes heating the source compounds of the respective elements separately and gradually forming the oxides (and may include forming mixed oxides). Further, the term "including an integration step and a heating step" means that steps of drying, pulverization, molding, and the like may be included in addition to the two steps.

In the second vapor phase catalytic oxidation method, the Bi source compound is bismuth subcarbonate which is water-insoluble and containing Mg, Ca, Zn, Ce, and/or Sm. The compound is preferably used in a powder form. The compounds as raw materials for catalyst production may consist of particles larger than the powder but preferably consist of small particles, considering the heating step for thermal diffusion. Thus, if the compounds as raw materials do not consist of small particles, the compounds are preferably pulverized before the heating step.

A specific example of the catalyst production method according to the second vapor phase catalytic oxidation method is as follows. Aqueous solutions of compounds of iron, cobalt, and nickel, preferably nitrates of the respective elements are added to a suitable aqueous solution of a molybdenum compound, preferably ammonium molybdate. Further, aqueous solutions of compounds of sodium, potassium, rubidium, thallium, boron, phosphorus, arsenic, and/or tungsten, preferably water-soluble salts of the respective elements are added to the mixture. Further, particulate or colloidal silica is added to the mixture if necessary. Next, bismuth subcarbonate powder containing a C component prepared in advance is added to the mixture. Bismuth subcarbonate containing a C component in advance is prepared as described above by: mixing bismuth and aqueous solutions such as Mg, Ca, Zn, Ce, and/or Sm, preferably aqueous solutions of nitrates of the respective elements; adding the aqueous solutions dropwise to an aqueous solution of ammonium carbonate or ammonium bicarbonate while mixing the whole; and washing the obtained slurry with water and the drying the slurry.

Next, the obtained slurry is sufficiently agitated, and then dried. The dried granule or cake product is subjected to heat treatment in air at 250 to 350° C. for a short period of time. Here, the obtained heat-treated product already contains salts of iron, cobalt, and nickel with acidic oxides, but contains bismuth subcarbonate mostly remained in a form of the raw material. This fact indicates that bismuth subcarbonate may be added at any time.

The obtained decomposed product is shaped into an arbitrary shape through methods such as extrusion molding, tablet compression, and support molding. The shaped product is then subjected to final heat treatment preferably at 450 to 650° C. for about 1 to 16 hours.

Further, the Sb—Mo catalyst preferably used in the second vapor phase catalytic oxidation method is the same as that represented by the general formula (II) in the above-mentioned multitube reactor of the present invention. The Sb—Mo catalyst used in the second vapor phase catalytic oxidation method is preferably produced using a mixed oxide represented by Sb—X—Si—O as a Sb source compound heated at 600 to 900° C.

Such a mixed oxide can be obtained by using: metal Sb, antimony oxide, or the like as an Sb source; nitrates, halides, or the like of the X elements as a raw material for an X component; and colloidal silica, particulate silica, or the like as an Si source; and subjecting a solid to heat treatment in the presence of molecular oxygen (such as air) at 600 to 900° C., preferably 650 to 850° C., the solid being obtained by, for example: adding the Sb source or Si source to an aqueous solution of an X component raw material; and evaporating the mixture to dryness under stirring.

Atomic ratios of the respective elements of the mixed oxide represented by $Sb_w\text{-}X_x\text{-}Si_y\text{-}O_z$ is $1 \leq w \leq 40$ (preferably $1 \leq w \leq 20$), $1 \leq x \leq 20$ (preferably $1 \leq x \leq 10$), and $1 \leq y \leq 10$ (preferably $1 \leq y \leq 5$). Note that, z is a value determined from an oxidation degree of the respective elements.

The Sb—Mo catalyst can be produced general production methods of a mixed oxide catalyst except that such a Sb mixed oxide is used.

The above-mentioned mixed oxide preferably accounts for at least 25%, preferably 50 to 100% of a final catalyst of the Sb—Mo catalyst.

A specific example of catalyst production involves wet mixing the thus-obtained Sb—X—Si—O mixed oxide powder with: multiple acids of Mo, V, or Nb (such as molybdic acid or phosphomolybdic acid) or salts thereof (such as ammonium salt); hydroxides or salts of those metals; and Y components (such as copper compound and tungsten compound). The production method further involves concentrating and drying the mixture, and then pulverizing the dried mixture.

The method for molding the catalyst, form, and shape of the catalyst used in the second vapor phase catalytic oxidation method are the same as those for the above-mentioned multitube reactor of the present invention.

Note that, the catalyst packed at the raw material gas inlet of the reaction tubes may have the same composition and form as, or may have different compositions and forms from, the catalyst packed at the outlet of the reaction tubes.

The second vapor phase catalytic oxidation method can be applied to any one of cases which performs a reaction employing two multitube reactors packed with different catalysts; and a reaction employing one reactor having a shell divided into two or more chambers by intermediate tube plates and having the respective chambers packed with different catalysts for obtaining (meth)acrylic acid at once, because (meth)acrylic acid production involves two-stage oxidation of propylene or isobutylene.

FIG. 5 shows a multitube reactor having a shell divided by the intermediate tube plate 9, and the second vapor phase catalytic oxidation method can be also applied to a method employing the reactor. Different heat mediums circulate in the respective divided spaces, and the spaces are controlled to different temperatures. A raw material gas may be introduced from either the port 4*a* or 4*b*. In FIG. 5, a flow direction of the heat medium inside the shell is indicated by arrows as an upflow, and thus, reference numeral 4*a* represents the raw material feed port in which the raw material gas process gas flows in a countercurrent to the heat medium. The raw material introduced from the raw material feed port 4*a* successively reacts inside the reaction tubes of the reactor.

The multitube reactor shown in FIG. 5 includes heat mediums having different temperatures in top and bottom areas (area A and area B in FIG. 5) of the reactor divided by the intermediate tube plate 9. The catalyst and the like inside the reaction tubes are packed in the same manner as in the above-mentioned multitube reactor of the present invention.

A mixed gas containing propylene, propane, or isobutylene with a molecular oxygen-containing gas is introduced from the raw material feed port 4*a* to the multitube reactor shown in FIG. 5 employed in the second vapor phase catalytic oxidation method, for example. First, the mixed gas is converted to (meth)acrolein in a first stage (reaction tubes in area A) for a former stage reaction, and the (meth)acrolein is then oxidized in a second stage (reaction tubes in area B) for a latter stage reaction, to thereby produce (meth)acrylic acid. A first stage portion of the reaction tubes (hereinafter, may also be referred to as "former stage portion") and a second stage portion of the reaction tubes (hereinafter, may also be referred to as "latter stage portion") are packed with different catalysts and are controlled to different temperatures for a reaction under optimum conditions. The inert substance not involved in the reaction is preferably packed in a portion where the intermediate tube plate exists between the former stage portion and the latter stage portion of the reaction tubes.

FIG. 6 is an enlarged view of the intermediate tube plate and the vicinity thereof. The former stage portion and the latter stage portion are controlled to different temperatures. However, precision of reaction temperature at lower temperatures tends to degrade when the temperature difference exceeds 100° C. because heat transfer from a high-temperature heat medium to a low-temperature heat medium cannot be neglected. In such a case, heat insulation is required above or below the intermediate tube plate for preventing the heat transfer. FIG. 6 shows a case employing a heat insulation board, and two to three thermal shields 10 are provided at positions of about 10 cm below or above the intermediate tube plate to form a flowless stagnant space 12 filled with the heat medium. It is preferable to produce a heat insulation effect thereby. Thermal shields 10 are fixed to the intermediate tube plate 9 by, for example, spacer rods 13.

The flow direction of the heat medium inside the shell is indicated by arrows as an upflow in FIGS. 1 and 5, but the second vapor phase catalytic oxidation method can also be applied to reactors having opposite directions of the heat medium. A direction of circulation flow of the heat medium must be set to prevent a phenomenon of engulfing, in the heat medium, a gas, specifically, an inert gas such as nitrogen existing on upper ends of the shell 2 and the circulating pump 7. The gas may be engulfed in an upflow heat medium in an upper portion inside the circulating pump 7 and a cavitation phenomenon may be caused inside the circulating pump, possibly resulting in a worst case of pump breakdown. The gas may also be engulfed in a downflow heat medium in an upper portion of the shell and a stagnant portion of a gas phase may form in an upper portion of the shell, thereby preventing cooling of the upper portion of the reaction tubes provided in the stagnant portion by the heat medium.

Prevention of gas stagnation requires of a degas line and replacing a gas in a gas phase with the heat medium. For that reason, inner pressure increase in the shell is tried by increasing a pressure of the heating medium in a heat medium feed line 8*a* and providing a heat medium draw line 8*b* at a highest position as possible. The heat medium draw line is preferably provided at least above a tube plate 5*a*.

In a multitube reactor oxidizing propylene, propane, or isobutylene with a molecular oxygen-containing gas, when the multitube reactor shown in FIG. 1 is employed, and a process gas is downflow, that is, when the raw material gas is introduced from the raw material gas inlet 4*a* and the products are discharged from the product discharging port 4*b* concentration of the target product, (meth)acrolein, is high and the process gas temperature increases through heating by the heat of reaction at the vicinity of the product discharging port 4*b* of the reactor. Thus, a heat exchanger is preferably provided after the product discharging port 4*b* of the reactor shown in FIG. 1, to thereby sufficiently cool the process gas and prevent an autooxidation reaction of (meth)acrolein.

Further, when the multitube reactor shown in FIG. 5 is employing, and a process gas is downflow, that is, when the raw material gas is introduced from the raw material gas inlet 4*a* and the products are discharged from the product discharging port 4*b* concentration of the target product, (meth)acrolein, is high in the vicinity of the intermediate tube plate 9 which is an end point of the first stage (reaction tubes in area A) and the process gas temperature increases through heating by the heat of reaction. If the catalyst is packed in the first stage alone (reaction tubes in area A: 5a-6a-6b-6a-9), a reaction is inhibited in the second stage of the reaction tubes 1b and 1c (reaction tubes in area B: between 9 and 5b) and the process gas is cooled by the heat medium flowing through a flow path to the shell, to thereby prevent an autooxidation reaction of (meth)acrolein. In this case, the reaction tubes 1b and 1c in area B (between 9 and 5b) are not packed with the catalyst, and the reaction tubes are left as cavities or packed with a solid without reaction activity. The latter is desirable for improving characteristics of heat transfer.

Further, catalyst layer temperature of the first stage becomes higher compared to the catalyst layer temperature of the second stage when packing different catalysts in the first stage (reaction tubes in area A: 5a-6a-6b-6a-9) and the second stage (reaction tubes in area B: 9-6a'-6b'-6a'-5b) of the multitube reactor shown in FIG. 5, obtaining (meth) acrolein from propylene, propane, or isobutylene in the first stage, and obtaining (meth) acrylic acid in the second stage. To be specific, the vicinity of the end point of the reaction (6a-9) in the first stage and the vicinity of the starting point of the reaction (9-6a') in the second stage have high temperatures. Thus, the reaction is inhibited in those portions and the process gas is cooled by the heat medium flowing through the flow path to the shell, to thereby prevent an autooxidation reaction of (meth)acrolein. In this case, the reaction tubes in the vicinity of the intermediate tube plate 9 (6a-9-6a' of reaction tubes 1b and 1c) are not packed with the catalyst, and the reaction tubes are left as cavities or packed with a solid without reaction activity. The latter is desirable for improving characteristics of heat transfer.

<Start Up Method of the Present Invention>

A gist of a start up method of the present invention is as follows. In a shell-tube type reactor circulating a heat medium which is solid at normal temperature, and having reaction tubes and an introducing port and a discharging port of a fluid flowing outside the reaction tubes for removing heat generated in the reaction tubes, the start up method is characterized by comprising: introducing a gas at a temperature in the range of 100 to 400° C. to the outside of the reaction tube to heat; and circulating the heat medium heated outside the reaction tube.

Hereinafter, the start up method of the present invention will be described with reference to the accompanying drawings. FIG. 13 is a process explanatory diagram showing an example of a preferable mode according to the start up method of the present invention.

The start up method of the present invention is a start up method for a shell-tube type reactor circulating a heat medium which is solid at normal temperature and having reaction tubes and an introducing port and a discharging port of a fluid flowing outside the reaction tubes for removing heat generated in the reaction tubes.

First, the shell-tube type reactor used in the start up method of the present invention is described. Any one of the conventionally known reactors may be employed as the shell-tube type reactor as long as the reactor employed has reaction tubes and an introducing port and a discharging port of a fluid flowing outside the reaction tubes for removing heat generated in the reaction tubes. Above all, a multitube reactor is preferable because the reactor provides a high reaction efficiency per a volume of the reactor.

A multitube reactor that can be used in the start up method of the present invention generally has the following structure. That is, tube plates are arranged on the top and bottom in the shell and a plurality of reaction tubes are equipped inside the shell with both ends of each reaction tube supported and fixed by the tube plates. Furthermore, an introducing port and a discharging port of a fluid flowing outside the reaction tubes of the shell are provided for removing heat generated in the reaction tubes. In the start up method of the present invention, shields may also be equipped for dividing the inside of the shell into multiple chambers.

Next, a description is given of a heat medium used as a fluid flowing outside the reaction tubes in the start up method of the present invention. The solidifying point of the heat medium is typically in the range of 50 to 250° C., preferably in the range of 130 to 180° C. Representative examples of such a heat medium include niter. Niter is particularly preferable because niter is excellent in thermal stability among the heat media used for controlling temperature in a chemical reaction and, in particular, has the most excellent stability to heat exchange at high temperatures ranging from 350 to 550° C.

Niter is the so-called molten salt and may adopt various compositions. Therefore, the solidifying point of niter varies depending on the compositions. However, niter of any composition can be suitably used in the start up method of the present invention as long as the niter has a solidifying point in the above range. Examples of a compound used as such niter include sodium nitrate, sodium nitrite, and potassium nitrate. Each of those compounds can be used alone or 2 or more types of them can be mixed before use.

Next, the characteristics of the start up method of the present invention will be described. In the start up method of the present invention, a gas at a temperature in the range of 100 to 400° C. is introduced to the outside of the reaction tubes to previously heat the inside of the reactor to a temperature equal to or higher than the solidifying point of the heat medium. That is, in the method described in the above-mentioned unexamined publication, a gas for heating a reactor is introduced into reaction tubes packed with a catalyst whereas, in the start up method of the present invention, the gas is introduced to the outside of the reaction tubes. This is a characteristic of the start up method of the present invention. A start up method for a reactor according to the start up method of the present invention does not adversely affect the catalyst. Preferable examples of the gas for heating a reactor include air.

Next, the above-mentioned heating method in the process shown in FIG. 13 will be described. In FIG. 13, a reactor represented by reference numeral (50) has a first chamber and a second chamber. In the example shown in the figure, a process gas is fed as a downflow while a heat medium is fed in an upflow. Lines (L1, L2, L3, and L4) constitute a process line, and lines (L6, L7, L8, L9, L10, L12, L13, and L14) constitute a heat medium line. Lines (L15 and L16) constitute a discharge line used during heating. In the figure, symbols ○●- and ●○- each represent a spectacle blind (SB), so-called partition. An SB is inserted into tubing to open and close a flow path. The former symbol represents an opened state, and the latter symbol represents a closed state.

First, an SB (61) is inserted into the line (L3) (that is, the flow path is closed) to close the feed line, used in ordinary operation, to the reaction tube (catalyst layer) of the reactor (50). Then, an SB (62) and an SB (63) are detached from the line (L5) (that is, the flow path is opened) to establish a line by the shell of the reactor (50) consisting of line (L1)→ blower (10)→line (L2)→line (L5)→line (L6)→heater (21)→line (L7) and line (L8)→tank (30)→line (L9). At this time, a valve (71) of the line (L5) is closed. Furthermore, an SB (64) of the line (L15) and a valve (72) of the line (L6) are opened to discharge the introduced gas.

Subsequently, the blower (10) is started, and the gas heated to a temperature in the range of 100 to 400° C. is introduced to the outside of the reaction tube of the reactor (50) by using the heater (21). The gas heats the reactor (50). The temperature inside the reactor (50) is preferably equal to or higher than the solidifying point of the heat medium subsequently circulated, and the temperature can be appropriately selected depending on the heat medium used. In general, it is sufficient to heat the shell of the reactor (50) to a temperature in the range of 150 to 250° C. This is because a temperature of the shell within the above range prevents resolidification of the heat medium even if the heat medium is fed after heating the shell since the heat medium has a solidifying point in the range of 50 to 250° C. At this time, it is preferable to keep the reaction tube (catalyst side) in an air atmosphere.

Subsequently, the blower (10) is stopped. The SB (62) of the line (L5) and the SB (63) of the line (L15) are closed. The valve (72) of the line (L16) is opened. Pumps (41 and 42) are started to introduce a heat medium into each of the first chamber (51) and second chamber (52) of the reactor (50) Then, the heat medium is circulated in each chamber by using an attached pump (43) to increase the temperature inside each chamber.

Each operation described above is preferably performed quickly, preferably within 1 hour. Too slow operation may cause resolidification of a heat medium when introducing the heat medium because the temperature of the shell decreases due to radiation of heat.

When heat exchange is performed by using a heat medium which is solid at normal temperature, the total amount of the heat medium is often recovered in the tank (30) after the use of the reactor (50). In such a case, the heat medium does not remain in the reactor (50) and is stored in the tank (30). Therefore, the heat medium in the tank (30) is heated by heaters (22 and 23) to an extent that the fluidity of the heat medium is ensured, and the heat medium is then introduced into the reactor (50).

The heat medium is introduced into the reactor (50) through 2 routes as described below. That is, the heat medium is fed to the first chamber (51) by the heat medium pump (41) of the tank (30) via the lines (L13, L14, L6, and L7). In addition, the heat medium is fed to the second chamber (52) by the heat medium pump (42) of the tank (30) through the lines (L12 and L10).

Then, the heat medium introduced into the reactor (50) is circulated inside each chamber by the attached pump (43). This is because the temperature inside the reactor (50) may not be increased to a target temperature only by introducing and circulating the heat medium heated in advance. In view of this, the heat medium is circulated, heated by the heater (21), and then introduced into the reactor (50) again. For example, the heat medium is discharged from the first chamber (51) and the line (L8) and is introduced into the reactor (50) by the pump (41) through the line (L7) via the heater (21).

In the case where the required temperature of the reactor (50) can be ensured through circulation of the heat-medium as described above, the production of a target product can be started by feeding a raw material gas to reaction tubes (catalyst side).

A start up method for a reactor according to the start up method of the present invention is particularly preferable as a start up method for a reactor used in the production of, for example, acrylic acid, methacrylic acid, acrolein, or methacrolein. This is because of the following reason. That is, acrylic acid or the like is a compound produced and used in a large amount, and a reactor becomes large in response to this. Therefore, it is particularly difficult to heat the reactor. The start up method of the present invention is particularly suitable for heating during start up of a large-scale reactor.

Acrylic acid is produced by: feeding propylene, propane, acrolein, or the like as a raw material gas to a conventionally known reactor packed with an oxidation catalyst; and allowing to react through a vapor phase catalytic oxidation reaction. In general, a raw material gas is allowed to coexist with given amounts of a molecular oxygen-containing gas and an inert gas and then a vapor phase catalytic oxidation reaction is carried out. For instance, when propylene is used as a raw material gas, acrolein is produced first. Then, acrolein is oxidized through vapor phase catalytic oxidation to yield acrylic acid.

Conventionally known oxidation catalysts can be used as former stage and latter stage catalysts in the 2-stage vapor phase catalytic oxidation reaction described above. Furthermore, a shape of the catalyst is not particularly limited and may be spherical, columnar, cylindrical, and the like. Furthermore, the catalyst may be diluted with a solid inert material when the catalyst is packed. Examples of such a solid inert material include α-alumina, alundum, mullite, carborundum, stainless steel, copper, aluminum, and ceramics.

In the present invention, it is possible to realize a more suitable vapor phase catalytic oxidation in the production of (meth) acrolein and/or (meth) acrylic acid by applying the above-mentioned first and second vapor phase catalytic oxidation methods and of the start up method of the present invention to the above-mentioned multitube reactor of the present invention.

That is, the vapor phase catalytic oxidation method using a multitube reactor of the present invention further comprising baffles connecting to the reaction tubes through connecting sites for changing a flow path of a heat medium introduced into the shell; circulating the heat medium through the outside of the of the reaction tubes; and feeding a raw material gas into the reaction tubes packed with a catalyst, to thereby obtain a reaction product gas, the vapor phase catalytic oxidation method comprising, determining catalyst packing specifications in the reaction tubes so that catalyst layer peak temperature sites of the reaction tubes are not located at the connecting sites between the baffles and the reaction tubes.

Such a vapor phase catalytic oxidation method is preferable for improving life of the catalyst packed inside the reaction tubes, preventing an yield of a target compound decreasing, preventing hot spot formation effectively, and performing a stable operation over a long period of time, without clogging the reaction tubes.

Further, in the present invention, the above-mentioned second vapor phase catalytic oxidation method can also be applied to such a vapor phase catalytic oxidation method. That is, propylene, propane, or isobutylene, and/or (meth) acrolein is oxidized through vapor phase catalytic oxidation with a molecular oxygen-containing gas by packing a Mo—Bi catalyst and/or a Sb—Mo catalyst to the reaction tube in such a manner that activity increases from the process gas inlet to process gas outlet of the reaction tube; and allowing a heat medium and a process gas to flow in a countercurrent.

Such a method for vapor phase catalytic oxidation method is preferable for improving life of the catalyst packed inside the reaction tubes, preventing an yield of a target product decreasing, preventing hot spot formation effectively, and performing a stable operation over a long period of time, without clogging the reaction tubes, and reducing the temperature of the process gas at the product discharging port of the reactor.

Further, in the present invention, the above-mentioned start up method of the present invention can also be applied to such a vapor phase catalytic oxidation method. That is, in a method comprising at least one of those vapor phase catalytic oxidation methods, the multitube reactor is stared up by: introducing a gas at a temperature in the range of 100 to 400° C. to the outside of the reaction tubes to heat; and circulating a heated heat medium which is solid at normal temperature through the outside of the reaction tubes.

Such a vapor phase catalytic oxidation method is preferable for starting up a reactor efficiently without affecting the activity of a catalyst adversely.

Although each of the reactor of the present invention and the reactor used in the vapor phase catalytic oxidation method of the present invention is limited to a multitube reactor equipped with a plurality of reaction tubes inside a single shell, the limitations are based on an industrial usage form. The present invention can also be applied to a single tube reactor and the single tube reactor also takes the same effect as those of the present invention.

BEST MODE FOR CARRYING OUT THE INVENTION

Figure 1:
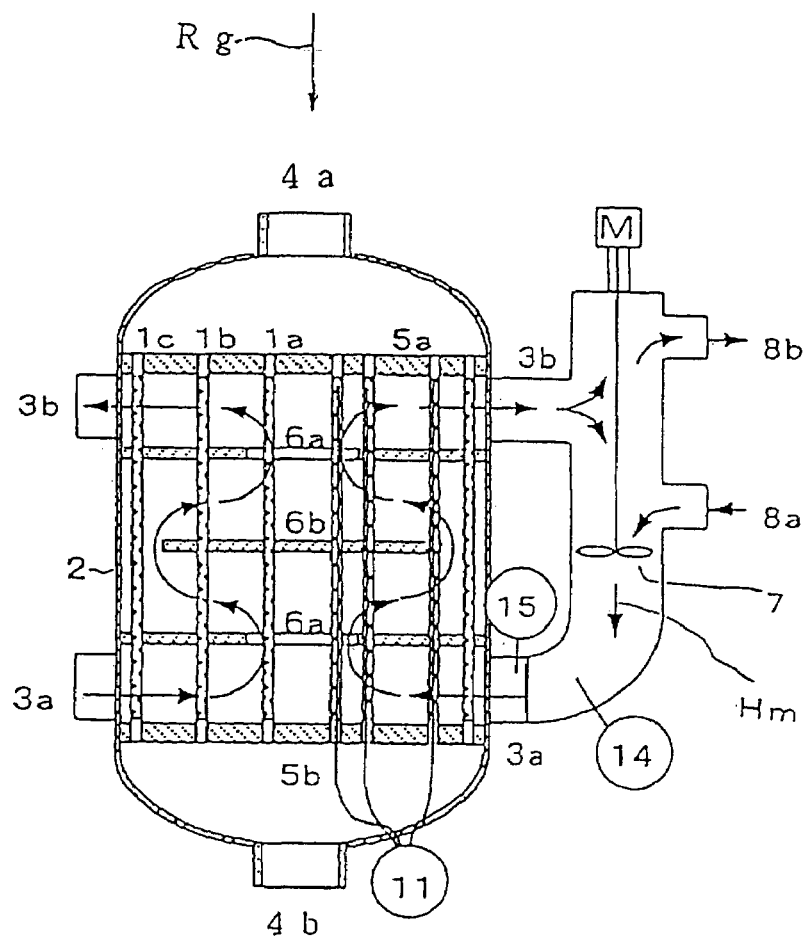
FIG. 1 is a sectional view of an example of a multitube reactor.
Figure 2:
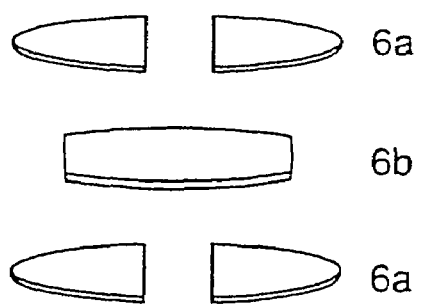
FIG. 2 is a perspective view of an example of baffles equipped inside a multitube reactor.
Figure 3:
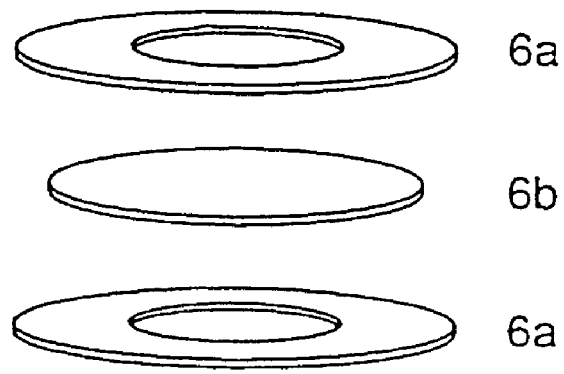
FIG. 3 is a perspective view of another example of baffles equipped inside a multitube reactor.
Figure 4:
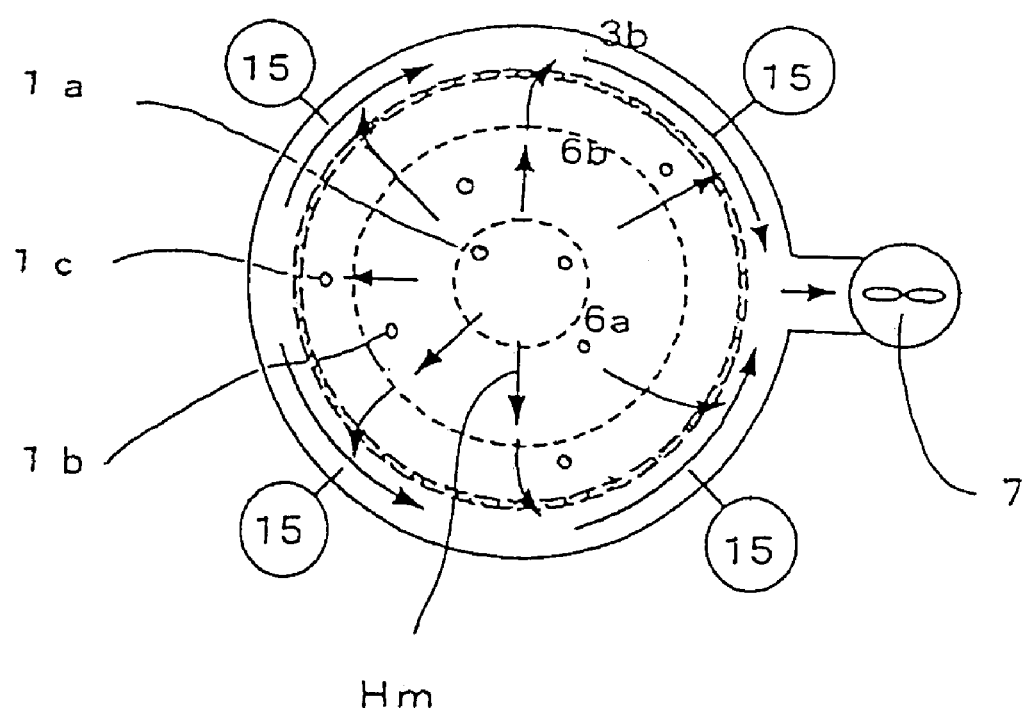
FIG. 4 is a view of the multitube reactor shown in FIG. 1 seen from above.
Figure 5:
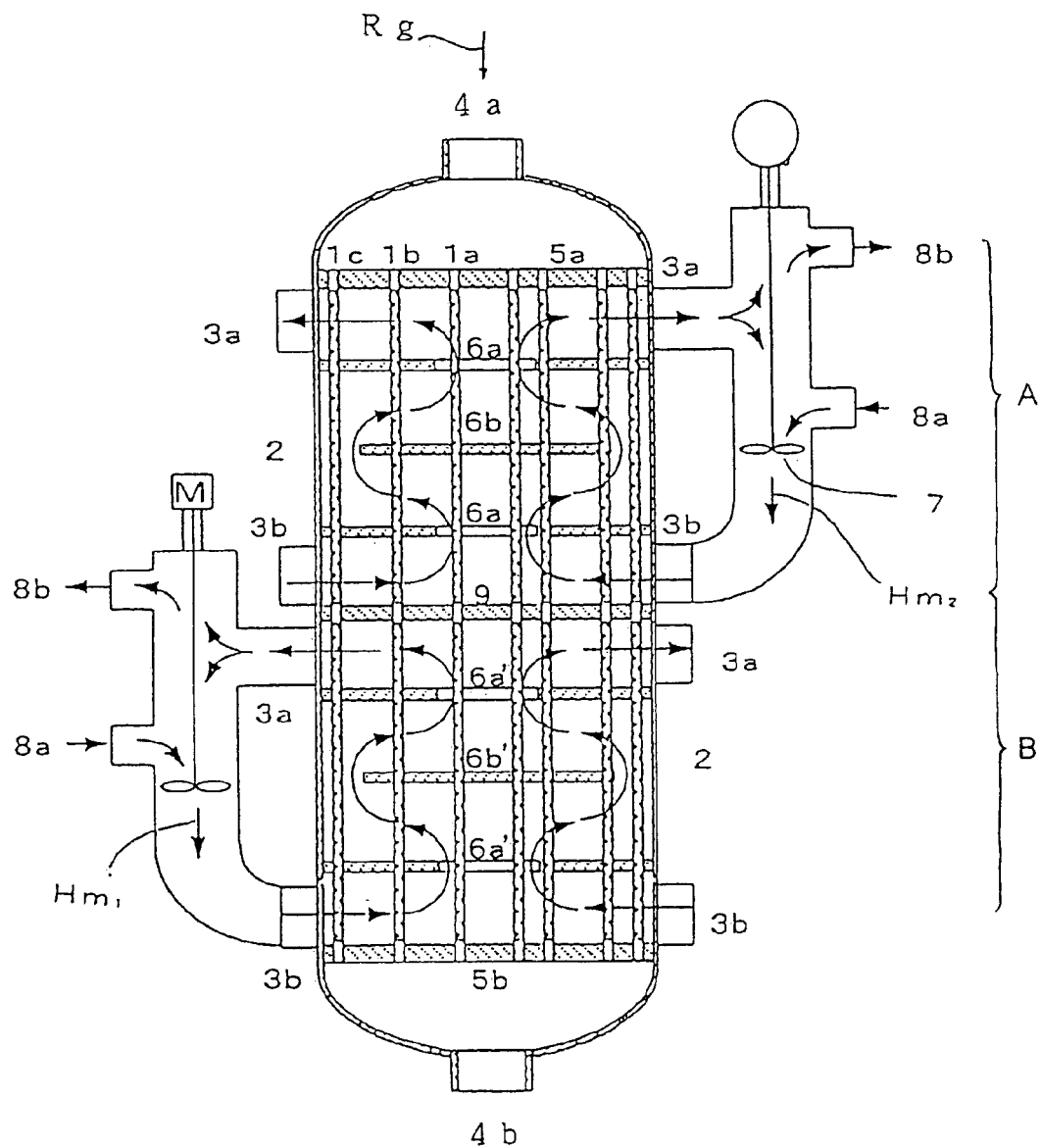
FIG. 5 is a sectional view of another example of a multitube reactor.
Figure 6:
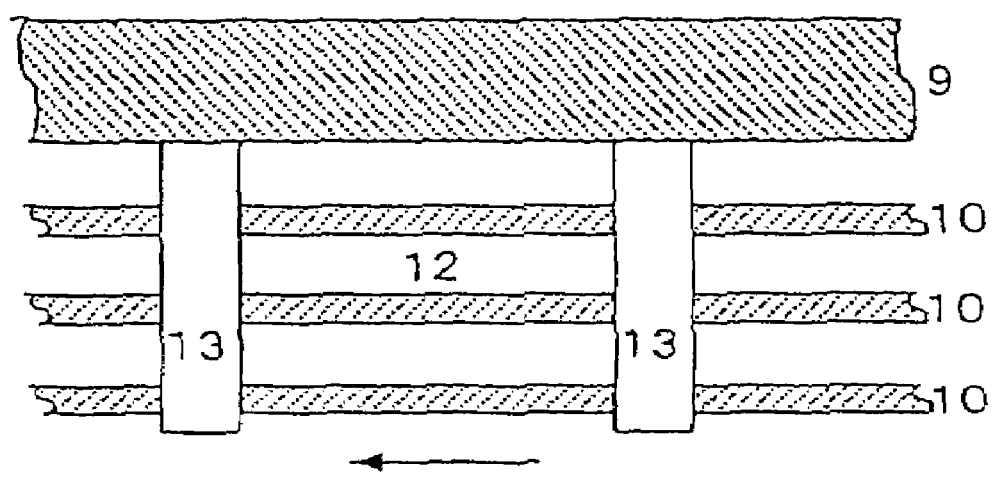
FIG. 6 is a fragmentary sectional view of an intermediate tube plate and thermal shields equipped inside the multitube reactor shown in FIG. 5.
Figure 7:
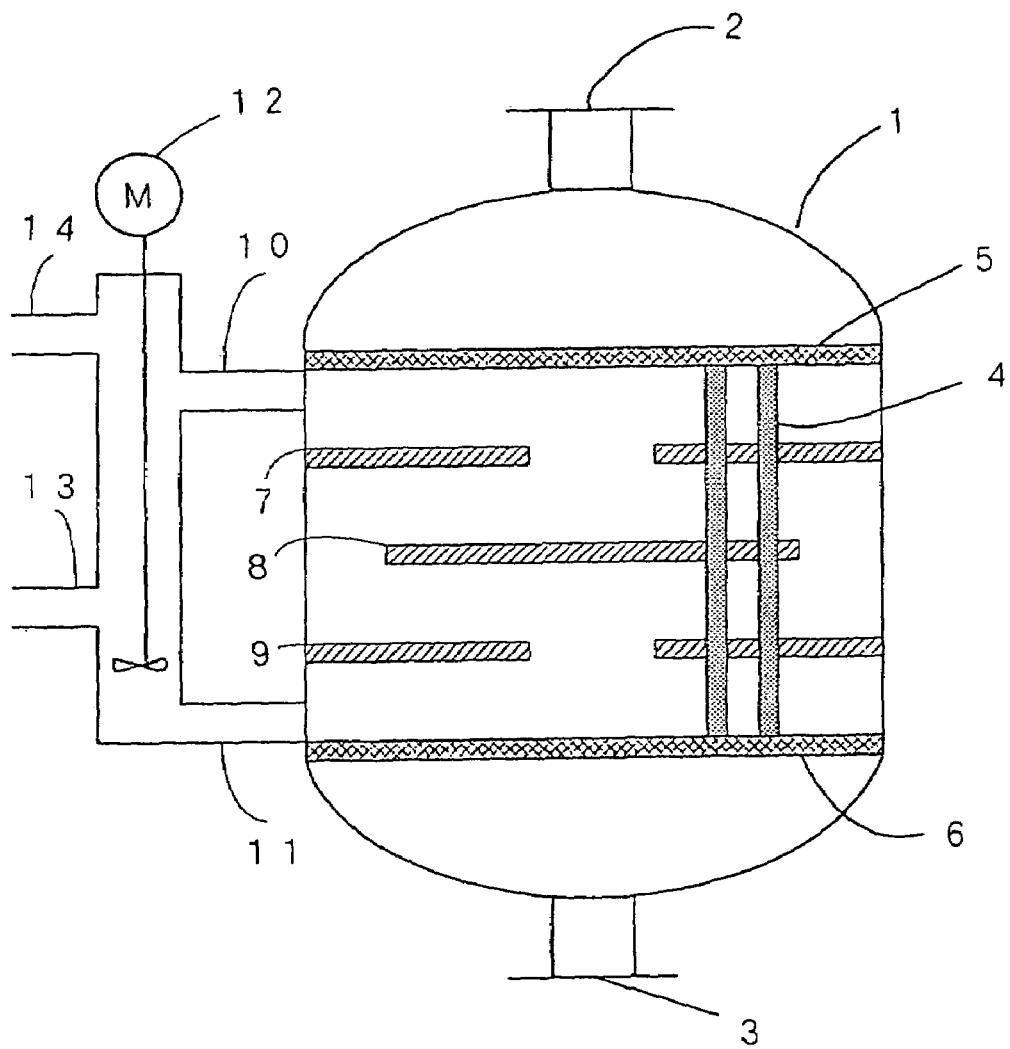
FIG. 7 is a diagram showing an embodiment of a fixed bed multitube heat-exchanger type reactor used in the first vapor phase catalytic oxidation method.
Figure 8:
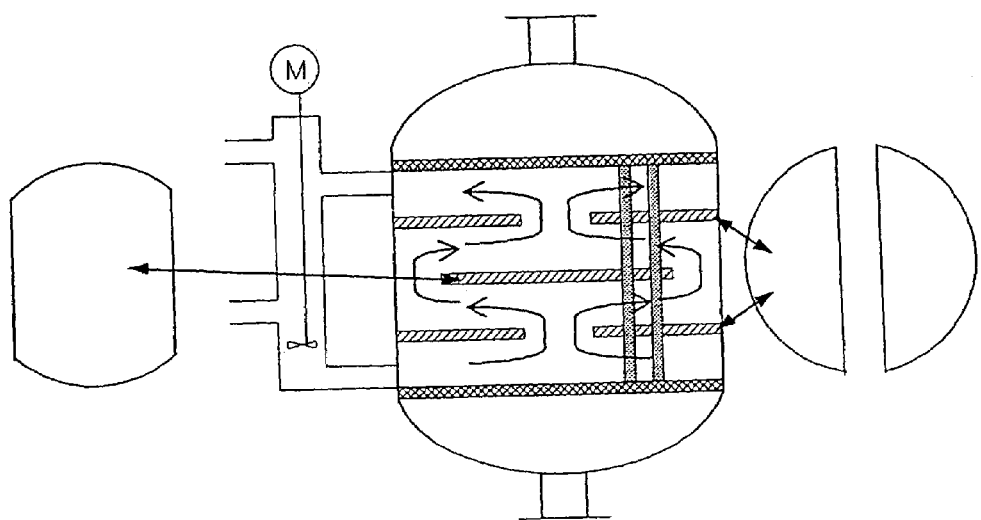
FIG. 8 is a diagram showing an embodiment of a fixed bed multitube heat-exchanger type reactor used in the first vapor phase catalytic oxidation method.
Figure 9:
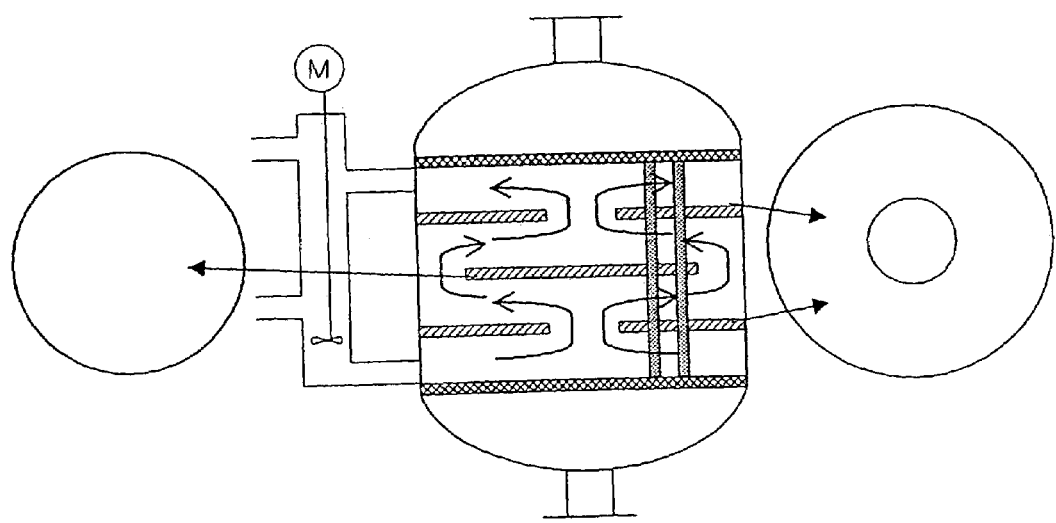
FIG. 9 is a diagram showing an embodiment of a fixed bed multitube heat-exchanger type reactor used in the first vapor phase catalytic oxidation method.
Figure 10:
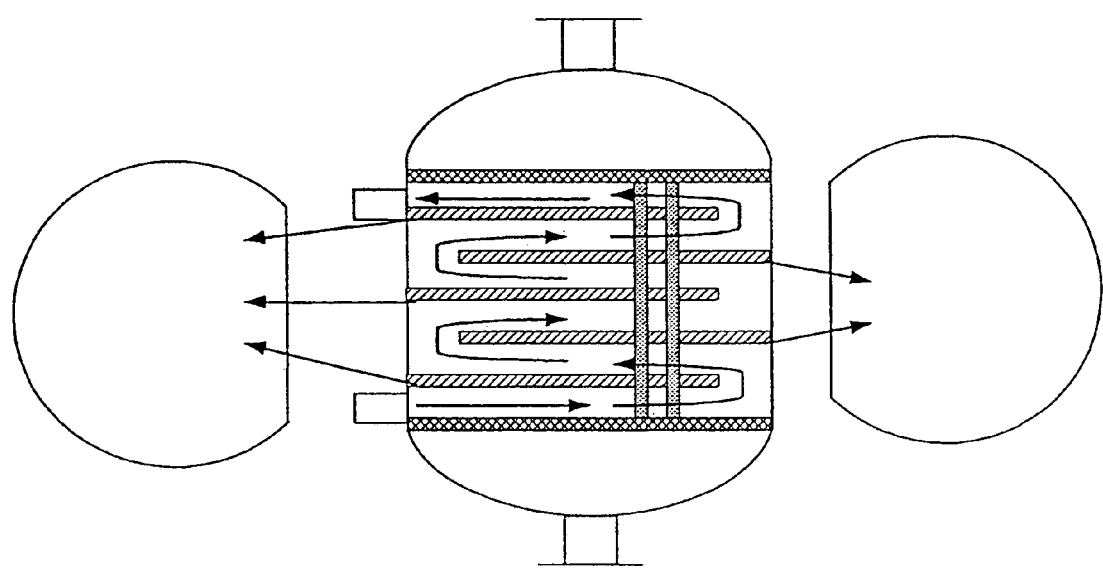
FIG. 10 is a diagram showing an embodiment of a fixed bed multitube heat-exchanger type reactor used in the first vapor phase catalytic oxidation method.
Figure 11:
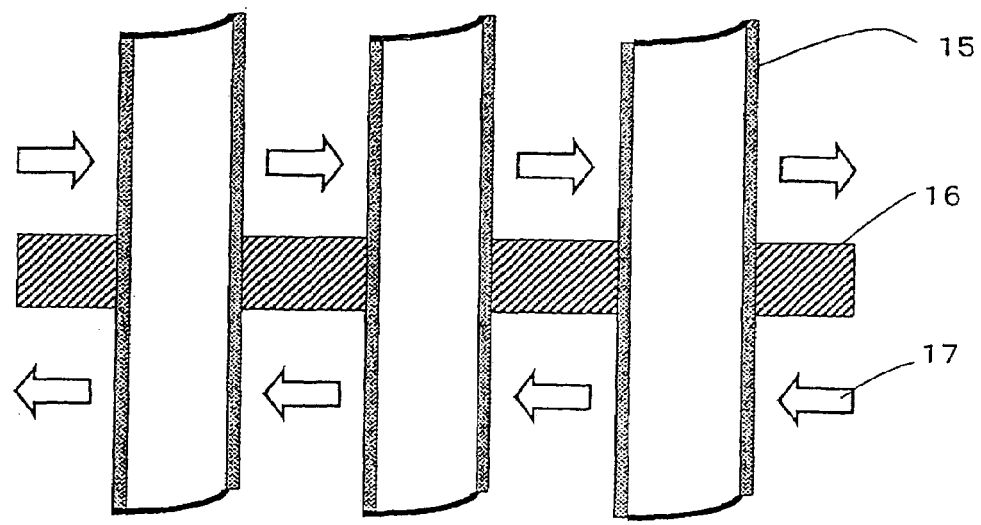
FIG. 11 is a diagram illustrating a state at connecting sites of baffles and reaction tubes of a fixed bed multitube heat-exchanger type reactor used in the first vapor phase catalytic oxidation method.
Figure 12:
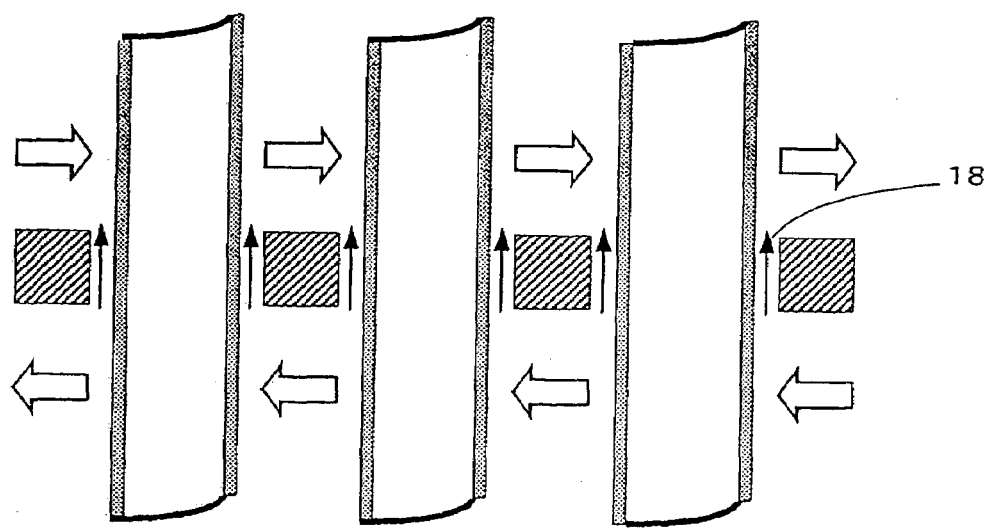
FIG. 12 is a diagram illustrating a state of connecting sites of baffles and reaction tubes of a fixed bed multitube heat-exchanger type reactor used in the first vapor phase catalytic oxidation method.

Hereinafter, the present invention will be further described in detail by examples, but the present invention is not limited by the examples so long as not departing from the gist of the invention.

EXAMPLE 1

For an oxidation reaction of propylene, catalyst powder having a composition (atomic ratio) of Mo(12)Bi(5)Ni(3)Co(2)Fe(0.4)Na(0.2)B(0.4)K(0.1)Si(24)O(x) was produced (oxygen composition x is a value determined from oxidation states of the respective metals) as a former stage catalyst.

The catalyst powder was molded in to ring-shaped catalysts having an outer diameter of 5 mmφ, an inner diameter of 2 mmφ, and a height of 4 mm.

Two stainless steel tubes both having a length of 3,500 mm, and respectively having an outside diameter of 30.57 mmΦ, a wall-thickness of 1.80 mm, and an outside diameter of 30.23 mmΦ, a wall-thickness of 2.10 mm were used as reaction tubes (nominal outside diameter of 30.40 mmΦ and nominal wall-thickness of 1.80 mm). Note that, an outside diameter tolerance and a wall-thickness tolerance of the tubes are ±0.17 mm (±0.56%) and +0.30 mm, −0 mm (+16.7%, −0%), respectively.

Further, a reactor used had a shell inner diameter of 100 mmΦ.

A nitrates-mixed molten salt niter was used as a heat medium Hm, and the heat medium was fed from a side of bottom of the shell.

Temperature of the niter fed to the shell was defined as reaction temperature. Further, a flow rate of the niter was adjusted so that a temperature difference between an outlet and inlet of the shell was 4° C.

Each of the reaction tubes was packed with 3,000 mm of the catalyst, and a raw material gas (Rg) containing 9 vol % propylene was fed from an upper portion of the shell at a gauge pressure of 75 kFa.

Temperature distributions in the reaction tubes were measured by inserting thereinto thermometers each having 10 points of measurement in an axial direction of the reaction tubes.

A reaction was conducted for 1 week at a heat medium Hm temperature of 330° C. A propylene conversion and an yield were 97.5% and 91.0%, respectively, and the highest temperature of reaction catalyst layers was 392° C.

The reaction was continued for 1 month maintaining the heat medium Hm temperature at 330° C. The propylene conversion and the yield were 97.0% and 90.5%, respectively, and the highest temperature of the reaction catalyst layers was 386° C.

EXAMPLE 2

Two stainless steel tubes both having a length of 3,500 mm, and respectively having an outside diameter of 30.58 mmΦ, a wall-thickness of 1.80 mm, and an outside diameter of 30.22 mmΦ, a wall-thickness of 2.14 mm were used as the reaction tubes (nominal outside diameter of 30.40 mmΦ and nominal wall-thickness of 1.80 mm). Note that, the outside diameter tolerance and the wall-thickness tolerance of the tubes are ±0.18 mm (±0.59%) and +0.34 mm, −0 mm (+18.9%, −0%), respectively.

The reaction was conducted in the same manner as in Example 1 except for the reaction tubes.

The reaction was conducted for 1 week at a heat medium Hm temperature of 330° C. The propylene conversion and the yield were 97.2% and 90.0%, respectively, and the highest temperature of the reaction catalyst layers was 394° C.

The reaction was continued for 1 month maintaining the heat medium Hm temperature at 330° C. The propylene conversion and the yield were 96.8% and 89.7%, respectively, and the highest temperature of the reaction catalyst layers was 389° C.

EXAMPLE 3

Two stainless steel tubes both having a length of 3,500 mm, and respectively having an outside diameter of 30.65 mmΦ, a wall-thickness of 1.80 mm, and an outside diameter of 30.15 mmΦ, a wall-thickness of 2.16 mm were used as the reaction tubes (nominal outside diameter of 30.40 mmΦ and nominal wall-thickness of 1.80 mm). Note that, the outside diameter tolerance and the wall-thickness tolerance of the tubes are ±0.25 mm (±0.82%) and +0.36 mm, −0 mm (+20%, −0%), respectively.

The reaction was conducted in the same manner as in Example 1 except for the reaction tubes.

The reaction was conducted for 1 week at a heat medium Hm temperature of 330° C. The propylene conversion and the yield were 97.4% and 89.9%, respectively, and the highest temperature of the reaction catalyst layers was 429° C.

The reaction was continued for 1 month maintaining the heat medium Hm temperature at 330° C. The propylene conversion and the yield were 94.0% and 88.0%, respectively, and the highest temperature of the reaction catalyst layers was 422° C.

As described above, improvement on life of the catalyst packed inside the reaction tubes and prevention of yield reduction of the target product could be realized by using the reaction tubes having an outside diameter tolerance of ±0.62% and a thickness tolerance of +19% to −0%.

EXAMPLE 4

Figure 14:
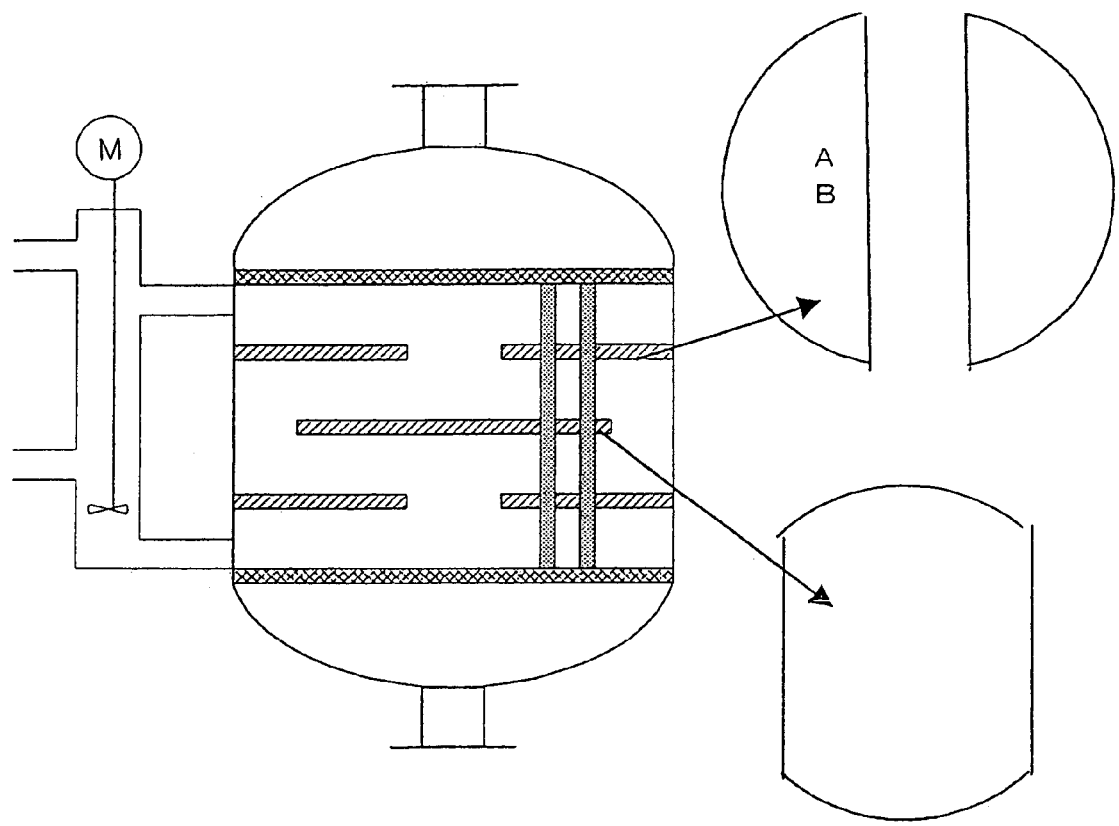
FIG. 14 is a schematic diagram illustrating Example 4.

A fixed bed multitube heat-exchanger type reactor shown in FIG. 14 which has 20,000 stainless steel reaction tubes having an inner diameter of 27 mm and a length of 5 m and double segment-type baffles for changing a flow path of the heat medium in the shell was used. Multi-point thermocouples were provided to allow measurement of catalyst layer temperature in the reaction tubes. Niter was used as the heat medium.

The reaction tube provided in position A in FIG. 14 was packed with alumina balls to a height of 1.7 m, a mixture containing 70% of an Mo—Bi—Fe catalyst prepared following a conventional procedure and 30% of alumina balls in volume ratio to a height of 3 m thereon, and alumina balls to a height of 0.3 m thereon.

A mixed gas consisting of 9 mol % of propylene, 71 mol % of air, 10 mol % of steam, nitrogen, and the like was fed in downflow under conditions of a contact time of 3 seconds. A temperature of the heat medium is 32° C. at this time.

The catalyst layer peak temperature site at this time was this side of a baffle (first baffle, that is, baffle higher in position of the baffles shown in FIG. 14) and the catalyst layer peak temperature was 400° C. Pressure loss increases of the reaction tube after 1-year operation and 2-year operation were 0.1 kPa and 0.15 kPa, respectively.

Here, the term "pressure loss increase" refers to a phenomenon of pressure increase inside the reaction tubes caused by a carbonization of reaction raw materials due to too high temperature to clog the reaction tubes. The pressure loss is determined by: feeding air or nitrogen of the same volume as the volume of gas fed during the reaction to the respective reaction tubes; and measuring the pressure of the reaction tube inlet.

EXAMPLE 5

The reaction tube provided in position B (next to A) in FIG. 14 was packed with alumina balls to a height of 1.5 m, a mixture containing 70% of the same catalyst as in Example 4 and 30% of alumina balls in volume ratio to a height of 3 m thereon, and alumina balls to a height of 0.5 m thereon.

The catalyst layer peak temperature site at this time was at a connecting site of the first baffle and the reaction tube, and the catalyst layer peak temperature was 415° C. The pressure loss increase of the reaction tube after 1-year operation was 0.5 kPa. The reaction tube was completely clogged after 2-year-operation, and the pressure loss increase could not be measured. As described above, the catalyst layer peak temperature site located at the connecting site causes excessive reaction and clogging of the reaction tube because removal of heat of reaction is insufficient, which is also apparent from high catalyst layer peak temperature.

As is clear from Examples 4 and 5, the present invention can provide a vapor phase catalytic oxidation method capable of effectively preventing hot spot formation and performing a stable operation over a long period of time and with long catalyst life, without clogging the reaction tubes by determining catalyst packing specifications in the reaction tubes so that the catalyst layer peak temperature sites inside the reaction tubes are not located at connecting sites between the baffles and the reaction tubes.

EXAMPLE 6

94 parts by weight of antimony paramolybdate was dissolved in 400 parts by weight of pure water by heating. Then, 7.2 parts by weight of ferric nitrate, 25 parts by weight of cobalt nitrate, and 38 parts by weight of nickel nitrate were dissolved in 60 parts by weight of pure water by heating. The two solutions were mixed with sufficient stirring.

Next, a solution prepared by dissolving 0.85 parts by weight of borax and 0.36 parts by weight of potassium nitrate in 40 parts by weight of pure water under heating was added to the slurry. Then, 64 parts by weight of particulate silica was added to the slurry, and the whole was mixed. Next, 58 parts by weight of bismuth subcarbonate mixed with 0.8 wt % Mg in advance was added to the mixture, and the whole was mixed under stirring. The slurry was subjected to drying by heating, and then to heat treatment in air at 300° C. for 1 hour. The obtained particulate solid was molded into tablets having a diameter of 5 mm and a height of 4 mm through tablet compression using a molding machine. The tablets were then baked at 500° C. for 4 hours, to thereby obtain a former stage catalyst.

The obtained catalyst was Mo—Bi mixed oxide having a composition ratio of catalyst powder of a composition of Mo(12)Bi(5)Ni(3)Co(2)Fe(0.4)Na(0.2)Mg(0.4)B(0.2)K(0.1)Si(24)O(x) (oxygen composition x is a value determined from oxidation states of the respective metals).

The multitube reactor used in this example was the same as that shown in FIG. 1. To be specific, the multitube reactor which has a shell (inner diameter of 4,500 mm) having 10,000 stainless steel reaction tubes having a length of 3.5 m and an inner diameter of 27 mm is used. The reaction tubes were not provided in a circular opening region at a center of the perforated disc-type baffle 6a having an opening portion in the vicinity of a central portion of the shell. The baffles were arranged such that the perforated disc-type baffle 6a having an opening portion in the vicinity of the central portion of the shell and the perforated disc-type baffle 6b provided to form an opening portion between the baffle and the outer peripheral portion of the shell were provided at even interval in an order of 6a-6b-6a, and an opening ratio of each of the baffles was 18%.

A nitrates-mixed molten salt (niter) was used as a heat medium, and the heat medium was fed from a lower portion of the reactor.

The catalysts packed in the reaction tubes were prepared by mixing the former stage catalyst and silica balls having a diameter of 5 mm and no catalytic activity, to thereby adjust the catalytic activity. The reaction tubes were packed with the catalysts so that the ratio of catalytic activity was 0.5, 0.7, and 1 from the reaction tube inlet.

The raw material gas was fed from an upper portion of the reactor, forming a countercurrent with the heat medium. A raw material gas consisting of 9 mol % of propylene, 15.1 mol % of molecular oxygen, 9 mol % of water, and 66.9 mol % of nitrogen was fed at a gauge pressure of 75 kPa (kilopascal). The temperature distributions in the reaction tubes were measured by inserting into the reaction tubes thermometers each having 10 points of measurement in an axial direction of the reaction tubes.

The reaction was conducted for 1 week at a heat medium temperature of 330° C. The propylene conversion was 97% and a total yield of acrolein and acrylic acid was 92%. The temperature of the niter fed was defined as the reaction temperature. The temperature difference of the niter between the inlet and outlet of the reactor was 4° C.

The propylene conversion and the yield were 96.8% and 91.9% respectively, after continuing the reaction for 1 month maintaining the heat medium temperature at 330° C.

The gas temperature at the reactor outlet was constant at about 330° C. during operation.

EXAMPLE 7

The reaction tubes were packed with catalysts in the same manner as in Example 6 using the catalysts used in Example 6.

The multitube reactor was used, which has a shell (inner diameter of 5,000 mm) having 9,500 stainless steel reaction tubes having a length of 3.5 m and an inner diameter of 27 mm. The reaction tubes were not provided in a circular opening region at a center of the perforated disc-type baffle 6a having an opening portion in the vicinity of a central portion of the shell. The baffles were the same as those used in Example 6, and were arranged such that the perforated disc-type baffle 6a having an opening portion in the vicinity of the central portion of the shell and the perforated disc-type baffle 6b provided to form an opening portion between the baffle and the outer peripheral portion of the shell were provided at even interval in an order of 6a-6b-6a, and an opening ratio of each of the baffles was 18%.

A nitrates-mixed molten salt (niter) was used as a heat medium, and this was fed from a lower portion of the reactor. The raw material gas consisting of 9 mol % of propylene, 15.1 mol % of molecular oxygen, 9 mol % of water, and 66.9 mol % of nitrogen was fed from the lower portion of the reactor (raw material feed port 4a) at a gauge pressure of 75 kPa (kilopascal), changing to a concurrent with the heat medium. Feed temperature of the heat medium was adjusted to obtain a propylene conversion of 97%, resulting in a feeding temperature of 333° C.

The yield was 91% 1 week after start of the operation, and the gas temperature at the reactor outlet was 337° C. at this time.

The reaction was continued, and after 10 days from the start of the operation, the gas temperature at an outlet portion of the reactor increased sharply from 337° C., and thus, the operation was stopped. After stopping the operation, the reactor was inspected. Black deposits were observed in the tube of the product discharging port 4b, and analysis thereof confirmed that the deposits were C contents.

As is clear from Examples 6 and 7, the process gas temperature can be reduced at the product discharging port of the reactor by packing the reaction tubes with the catalysts so that the catalytic activity increases-from the process gas inlet to the process gas outlet of reaction tubes.

EXAMPLE 8

Figure 13:
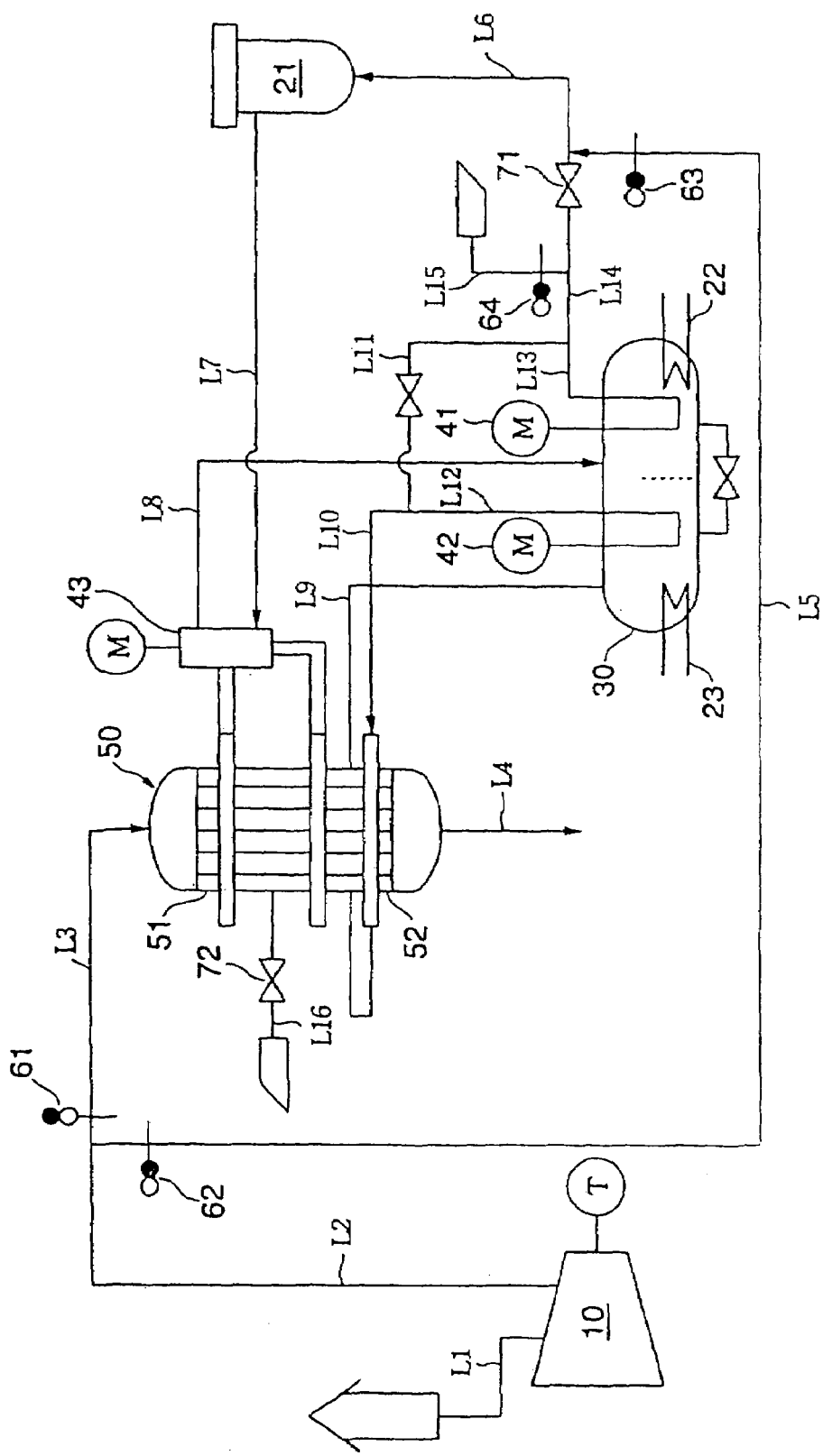
FIG. 13 is a process explanation diagram showing an example of a preferable embodiment of a start up method of the present invention.

The multitube reactor was started up by using: the process shown in FIG. 13; niter as a heat medium composed of 40 wt % sodium nitrite, 7 wt % sodium nitrate, and 53 wt % potassium nitrate; and air as a gas for heating introduced outside the reactor. Note that, the niter was stored in a tank and was not remained inside the reactor before the start up. Further, the multitube reactor used was an oxidation reactor having an inner diameter of 4,500 mm and had a structure including 13,000 reaction tubes having a length of 4,000 mm supported by an upper tube plate and a lower tube plate. Further, a shield was provided at a position 300 mm from a lower portion of the reactor to divide the reactor into two chambers.

First, SBs (61) and (62) of respective lines (L3) and (L5) were switched, to change a line from a blower (10) into a reactor (50), to a line from the blower (10) to a heater (21). The blower (10) was then started. Air was fed at a rate of 6 t/hr to the heater (21) for preheating to 250° C., and the heated air was fed to the oxidation reactor (50) via a line (L7) and/or line (L8) to a tank (30) and then to a line (L9).

The blower (10) was stopped when the temperature of the reactor (50) reached 230° C., and the above SBs were switched. Then, a heat medium heated to 200° C. in advance by heaters (22) and (23) were fed from the tank (30) with pumps (41) and (42). The heat medium was fed to a first chamber (51) via lines (L13), (L14), (L6), and (L7) with the pump (41). The heat medium was fed to a second chamber (52) via lines (L12) and (L10) with the pump (42).

A pump (43) was then started after the heat medium was introduced into the reactor (50), to circulate the heat medium inside the first chamber (51). The temperature of the first chamber (51) was adjusted by feeding the heat medium from the reactor (50) to the heater (21) via lines (L8), (L13), (L14), and (L6) and circulating the heat medium to the reactor (50) via line (L7) The temperature of the second chamber (52) was adjusted with the heater (23) attached to the tank (30).

The heat medium temperatures of the first chamber (51) and the second chamber (52) were 330° C. and 230° C., respectively, reaching predetermined reaction temperatures. Thus, the heater (21) was stopped, and the start up was completed. The start up took 40 hours.

EXAMPLE 9

A shell and tube type reactor having the following structure was used. That is, the reactor had a stainless. steel double-tube reaction tubes with an inner tube having an inner diameter of 24 mm and a length of 3.5 m. The inner tube was packed with a catalyst having a composition of Mo(12)Bi(5)Ni(3)Co(2)Fe(0.4)Na(0.2)B(0.4)K(0.1)Si(24)O(x) (oxygen composition x is a value determined from oxidation states of the respective metals). A region between the inner tube and an outer tube was filled with niter as the heat medium so that uniform temperature was maintained by stirring.

Instrumented air was fed to the reactor at a rate of 1 Nl/hr and the shell was maintained at 250° C. for 40 hours. Then, the niter at 330° C. was circulated, and the raw material gas containing 9 vol % of propylene as a raw material was fed to the reactor. The propylene conversion was 97% and the total yield of acrolein and acrylic acid was 92%.

EXAMPLE 10

The reaction was conducted in the same manner as in Example 9 except that nitrogen heated to 250° C. was fed to the inner tube (catalyst layer) at a rate of 20 l/hr for 40 hours. Here, the niter temperature had to be increased to 340° C. to obtain a propylene conversion of 97%.

EXAMPLE 11

The reaction was conducted in the same was as in Example 9 except that air heated to 250° C. was fed to the inner tube (catalyst layer) at a rate of 20 Nl/hr for 40 hours. In Example 11, the activity of the catalyst changed provoking a reaction out of control, and the reaction had to be stopped.

As is clear from Examples 8, 9, 10, and 11, the reactor can be started up effectively without adversely affecting the catalytic activity by: introducing heated gas to the outside of the reaction tubes packed with the catalysts to heat the catalyst; and circulating the heated heat medium to the outside of the reaction tubes.

INDUSTRIAL APPLICABILITY

According to the present invention, in a multitube reactor and a method for producing (meth) acrylic acid which uses the reactor, tube products having a nominal outside diameter tolerance and a nominal wall-thickness tolerance of ±0.62% and +19% to −0% respectively, particularly preferably ±0.56% and +17% to −0% respectively, which are more rigorous than the tolerances of the present engineering specification JIS or ASTM, were used as the reaction tubes equipped inside the shell of the reactor. As a result, the present invention enables (meth)acrylic acid production from propylene or isobutylene while effectively preventing a reaction out of control and advanced catalyst deterioration and producing (meth)acrylic acid stably at a high yield over a long period of time.

The present invention provides a vapor phase catalytic oxidation method of obtaining a reaction product gas capable of effectively preventing hot spot formation and performing a stable operation at a high yield of a reaction product gas over a long period of time and with long catalyst life, without clogging the reaction tubes by: using a fixed bed multitube heat-exchanger type reactor having a plurality of reaction tubes and baffles for changing a flow path of the heat medium; circulating the heat medium through the outside of the reaction tubes; and feeding the raw material gas inside the reaction tubes packed with a catalyst.

The present invention provides a multitube reactor and a vapor phase catalytic oxidation method capable of reducing the product temperature, preventing autooxidation of the product, obtaining the product in high yield, and preventing equipment breakdown due to abnormal increase of temperature through autooxidation by: allowing the heat medium circulating to flow in the multitube reactor and the process gas in a countercurrent, that is, in opposite directions; and packing the reaction tubes with a specific catalyst.

The present invention provides an efficient start up method for a shell-tube type reactor circulating a heat medium which is solid at normal temperature, without adversely affecting the catalytic activity. The present invention is significantly valuable industrially.

Further, the present invention can actualize the multitube reactor or the vapor phase catalytic oxidation method employing the multitube reactor exerting the plurality of above-mentioned significant effects.

The invention claimed is:

1. A vapor phase catalytic oxidation method comprising: providing a multitube reactor comprising a plurality of reaction tubes having a catalyst packed therein, and a shell equipped with the reaction tubes inside and into which a heat medium flowing outside the reaction tubes is introduced, wherein the reaction tubes are selected from tubes having same nominal outside diameter and same nominal wall-thickness, an outside diameter tolerance of ±0.62%, and a wall-thickness tolerance of +19% to −0%, which further comprises baffles connected to the reaction tubes through connecting sites for changing a flow path of a heat medium introduced into the shell; circulating the heat medium through the outside of the reaction tubes; and feeding a reaction raw material gas inside the reaction tubes packed with a catalyst to obtain reaction product gas; wherein the method comprises setting catalyst packing specifications in the reaction tubes so that catalyst layer peak temperature sites of the reaction tubes are not located at the connecting sites between the baffles and the reaction tubes.

2. A vapor phase catalytic oxidation method comprising: providing a multitube reactor comprising a plurality of reaction tubes having a catalyst packed therein, and a shell equipped with the reaction tubes inside and into which a heat medium flowing outside the reaction tubes is introduced, wherein the reaction tubes are selected from tubes having same nominal outside diameter and same nominal wall-thickness, an outside diameter tolerance of ±0.56%, and a wall-thickness tolerance of +17% to −0%, which further comprises baffles connected to the reaction tubes through connecting sites for changing a flow path of a heat medium introduced into the shell; circulating the heat medium through the outside of the reaction tubes; and feeding a reaction raw material gas inside the reaction tubes packed with a catalyst to obtain reaction product gas; wherein the method comprises setting catalyst packing specifications in the reaction tubes so that catalyst layer peak temperature sites of the reaction tubes are not located at the connecting sites between the baffles and the reaction tubes.

3. The vapor phase catalytic oxidation method according to claim 1, wherein the method comprises: packing the reaction tubes with a Mo—Bi catalyst and/or Sb—Mo catalyst so that an activity increases from a process gas inlet to a process gas outlet of the reaction tubes; allowing the heat medium and the process gas to flow in a countercurrent; and oxidizing propylene, propane, or isobutylene, and/or (meth)acrolein through vapor phase catalytic oxidation with a molecular oxygen-containing gas.

4. The vapor phase catalytic oxidation method according to claim 2, wherein the method comprises: packing the reaction tubes with a Mo—Bi catalyst and/or Sb—Mo catalyst so that an activity increases from a process gas inlet to a process gas outlet of the reaction tubes; allowing the heat medium and the process gas to flow in a countercurrent; and oxidizing propylene, propane, or isobutylene, and/or (meth)acrolein through vapor phase catalytic oxidation with a molecular oxygen-containing gas.

5. The vapor phase catalytic oxidation method according to claim 1, wherein the method comprises: heating the reaction tubes through introduction of a gas having temperature of 100 to 400° C. outside the reaction tubes; and circulating the heat medium which is solid at normal temperature outside the heated reaction tubes to start up the multitube reactor.

6. The vapor phase catalytic oxidation method according to claim 2, wherein the method comprises: heating the reaction tubes through introduction of a gas having temperature of 100 to 400° C. outside the reaction tubes; and circulating the heat medium which is solid at normal temperature outside the heated reaction tubes to start up the multitube reactor.

7. A vapor phase catalytic oxidation method comprising: using a fixed bed multitube heat-exchanger type reactor having a plurality of reaction tubes and baffles connected to the reaction tubes through connecting sites for changing a flow path of a heat medium flowing outside the reaction tubes; circulating the heat medium through the outside of the reaction tubes; feeding a reaction raw material gas inside the reaction tubes packed with a catalyst to obtain a reaction product gas, wherein the method comprises setting catalyst packing specifications in the reaction tubes so that catalyst layer peak temperature sites of the reaction tubes are not located at the connecting sites between the baffles and the reaction tubes.

8. The vapor phase catalytic oxidation method according to claim 7, wherein layers having different catalyst packing specifications are provided with at least two or more in one reaction tube.

9. The vapor phase catalytic oxidation method according to claim 7, wherein items for setting the catalyst packing specifications comprise a type of the catalyst, an amount of the catalyst, a form of the catalyst, a method for diluting the catalyst, and lengths of reaction zones.

10. The vapor phase catalytic oxidation method according to claim 7, wherein the method comprises oxidizing propane, propylene, and/or isobutylene with molecular oxygen through the vapor phase catalytic oxidation method to produce (meth)acrylic acid.

11. A vapor phase catalytic oxidation method comprises: using a multitube reactor which comprises: a cylindrical shell having a raw material feed port and a product discharging port; a plurality of ring-shaped tubes arranged on an outer periphery of the cylindrical shell for introducing or discharging a heat medium into or from the cylindrical shell; a circulating device connecting the plurality of the ring-shaped tubes one another; a plurality of reaction tubes restrained by a plurality of tube plates of the reactor and comprising a catalyst; and a plurality of baffles provided in a longitudinal direction of the reactor and for changing a direction of the heat medium introduced into the cylindrical shell; oxidizing propylene, propane, or isobutylene, and/or (meth)acrolein through vapor phase catalytic oxidation with a molecular oxygen-containing gas to obtain (meth)acrolein and/or (meth)acrylic acid,; wherein the method comprises,
    packing a Mo—Bi catalyst and/or Sb—MO catalyst in the reaction tubes so that anactivity increases from a process gas inlet to a process gas outlet of the reaction tubes; and
    allowing the heat medium and the process gas to flow in a countercurrent.

12. The vapor phase catalytic oxidation method according to claim 11, wherein the Mo—Bi catalyst is represented by the following general formula (I) and the Sb—Mo catalyst is represented by the following general formula (II):

$$Mo_aW_bBi_cFe_dA_eB_fC_gD_hE_iO_j \qquad (I)$$

(wherein, Mo represents molybdenum; W represents tungsten; Bi represents bismuth; Fe represents iron; A represents at least one type of element chosen from nickel and cobalt; B represents at least one type of element selected from the group consisting of sodium, potassium, rubidium, cesium, and thallium; C represents at least one type of element selected from alkaline earth metals; D represents at least one type of element selected from the group consisting of phosphorus, tellurium, antimony, tin, cerium, lead, niobium, manganese, arsenic, boron, and zinc; E represents at least one type of element selected from the group consisting of silicon, aluminum, titanium, and zirconium; O represents oxygen; a, b, c, d, e, f, g, h, i, and j represent atomic ratios of Mo, W, Bi, Fe, A, B, C, D, E, and O respectively; and if a=12, $0 \leq b \leq 10$, $0 < c \leq 10$, $0 < d \leq 10$, $2 \leq e \leq 15$, $0 < f \leq 10$, $0 \leq g \leq 10$, $0 \leq h \leq 4$, and $0 \leq i \leq 30$; and j is a value determined from oxidation states of the respective elements); and $$Sb_kMO_l(V/Nb)_mX_nY_pSi_qO_r \qquad (II)$$

(wherein, Sb represents antimony; Mo represents molybdenum; V represents vanadium; Nb represents niobium; X represents at least one type of element selected from the group consisting of iron (Fe), cobalt (Co), nickel (Ni), and bismuth (Bi); Y represents at least one type of element chosen from copper (Cu) and tungsten (W); Si represents silicon; O represents oxygen; (V/Nb) represents V and/or Nb; k, l, m, n, p, q, and r represent atomic ratios of Sb, Mo, (V/Nb), X, Y, Si, and O respectively; and $1 \leq k \leq 100$, $1 \leq l \leq 100$, $0.1 \leq m \leq 50$, $1 \leq n \leq 100$, $0.1 \leq p \leq 50$, $1 \leq q \leq 100$; and r is a value determined from oxidation states of the respective elements).

* * * * *